US012613212B2

(12) United States Patent
Rognrud et al.

(10) Patent No.: US 12,613,212 B2
(45) Date of Patent: Apr. 28, 2026

(54) NON-INVASIVE BLADDER CANCER DETECTION SYSTEM VIA LIQUID AND GASEOUS PHASE ANALYSIS

(71) Applicant: REGENTS OF THE UNIVERSITY OF MINNESOTA, Minneapolis, MN (US)

(72) Inventors: Christopher Brian Rognrud, Blaine, MN (US); Vijay Koya, Blaine, MN (US); August Judisch, Minneapolis, MN (US); Anthony Frank Tassoni, Jr., Andover, MN (US); Gregory J. Sherwood, White Bear Lake, MN (US); Kate Louise Frost, New Brighton, MN (US); Justin Theodore Nelson, Vadnais Heights, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 914 days.

(21) Appl. No.: 17/242,750

(22) Filed: Apr. 28, 2021

(65) Prior Publication Data

US 2021/0341409 A1     Nov. 4, 2021

Related U.S. Application Data

(60) Provisional application No. 63/018,704, filed on May 1, 2020.

(51) Int. Cl.
B01L 3/00 (2006.01)
G01N 27/22 (2006.01)
(Continued)

(52) U.S. Cl.
CPC ............ *G01N 27/227* (2013.01); *B01L 3/508* (2013.01); *G01N 33/54373* (2013.01); (Continued)

(58) Field of Classification Search
CPC ........... G01N 27/227; G01N 33/54373; G16H 70/60; G16H 10/40; G16H 50/20; B01L 3/508; B01L 2200/06; B01L 2300/0663
See application file for complete search history.

(56) References Cited

U.S. PATENT DOCUMENTS 3,661,528 A     5/1972  Falk
3,952,730 A     4/1976  Key
(Continued)

FOREIGN PATENT DOCUMENTS

CA         2673142         4/2008
CA         2800887         12/2011
(Continued)

OTHER PUBLICATIONS

"First Office Action," for Chinese Patent Application No. 201880032911.9 mailed Nov. 3, 2021 (11 pages) with English Summary.
(Continued)

*Primary Examiner* — Charles Capozzi
*Assistant Examiner* — Michael Stanley Gzybowski
(74) *Attorney, Agent, or Firm* — Pauly, DeVries Smith & Deffner LLC

(57)                ABSTRACT

Embodiments herein relate to non-invasive bladder cancer detection systems and methods. In an embodiment, a method for detecting a disease state in a subject is included. The method includes obtaining a liquid biological sample from the subject and placing it into a container and contacting the liquid biological sample with a first chemical sensor element, where the first chemical sensor element can include a plurality of discrete graphene varactors. The method can include sensing and storing capacitance of each of the discrete graphene varactors to obtain a first sample data set. Other embodiments are also included herein.

4 Claims, 15 Drawing Sheets

(51) Int. Cl.

| | |
|---|---|
| *G01N 33/543* | (2006.01) |
| *G16H 10/40* | (2018.01) |
| *G16H 50/20* | (2018.01) |
| *G16H 70/60* | (2018.01) |

(52) U.S. Cl.
CPC ............. *G16H 10/40* (2018.01); *G16H 50/20* (2018.01); *G16H 70/60* (2018.01); *B01L 2200/06* (2013.01); *B01L 2300/0663* (2013.01)

(56) References Cited

U.S. PATENT DOCUMENTS

| | | | |
|---|---|---|---|
| 3,981,297 A | 9/1976 | Dunn et al. | |
| 4,820,011 A | 4/1989 | Umegaki et al. | |
| 4,901,727 A | 2/1990 | Goodwin | |
| 5,174,290 A | 12/1992 | Fiddian-Green | |
| 5,186,172 A | 2/1993 | Fiddian-Green | |
| 5,357,971 A | 10/1994 | Sheehan et al. | |
| 5,423,320 A | 6/1995 | Salzman et al. | |
| 5,494,831 A | 2/1996 | Kindler | |
| 5,704,368 A | 1/1998 | Asano et al. | |
| 5,834,626 A | 11/1998 | De Castro et al. | |
| 5,928,155 A | 7/1999 | Eggers et al. | |
| 6,006,121 A | 12/1999 | Vantrappen et al. | |
| 6,029,076 A | 2/2000 | Fiddian-Greene et al. | |
| 6,085,576 A | 7/2000 | Sunshine et al. | |
| 6,149,624 A | 11/2000 | McShane | |
| 6,170,318 B1 | 1/2001 | Lewis | |
| 6,192,168 B1 | 2/2001 | Feldstein et al. | |
| 6,238,339 B1 | 5/2001 | Fiddian-Greene et al. | |
| 6,248,078 B1 | 6/2001 | Risby et al. | |
| 6,312,390 B1 | 11/2001 | Phillips et al. | |
| 6,480,734 B1 | 11/2002 | Zhang et al. | |
| 6,599,253 B1 | 7/2003 | Baum et al. | |
| 6,615,066 B2 | 9/2003 | Huyberechts et al. | |
| 6,712,770 B2 | 3/2004 | Lin et al. | |
| 6,726,637 B2 | 4/2004 | Phillips et al. | |
| 6,733,464 B2 | 5/2004 | Olbrich et al. | |
| 6,781,690 B2 | 8/2004 | Armstrong et al. | |
| 6,955,652 B1 | 10/2005 | Baum et al. | |
| 6,978,182 B2 | 12/2005 | Mazar et al. | |
| 7,032,431 B2 | 4/2006 | Baum et al. | |
| 7,123,359 B2 | 10/2006 | Armstrong et al. | |
| 7,177,686 B1 | 2/2007 | Turcott et al. | |
| 7,387,010 B2 * | 6/2008 | Sunshine ........... | G01N 33/0073 |
| | | | 340/505 |
| 7,426,848 B1 | 9/2008 | Li et al. | |
| 7,459,312 B2 | 12/2008 | Chen et al. | |
| 7,704,214 B2 | 4/2010 | Meixner et al. | |
| 7,809,441 B2 | 10/2010 | Kane et al. | |
| 7,871,572 B2 | 1/2011 | Yang et al. | |
| 7,955,562 B2 | 6/2011 | Hong et al. | |
| 7,972,277 B2 | 7/2011 | Oki et al. | |
| 7,988,917 B2 | 8/2011 | Roesicke et al. | |
| 7,992,422 B2 | 8/2011 | Leddy et al. | |
| 8,043,860 B2 | 10/2011 | Leznoff et al. | |
| 8,052,933 B2 | 11/2011 | Schirmer et al. | |
| 8,080,206 B2 | 12/2011 | Leddy et al. | |
| 8,124,419 B2 | 2/2012 | Grigorian et al. | |
| 8,153,439 B2 | 4/2012 | Zamborini et al. | |
| 8,154,093 B2 | 4/2012 | Passmore et al. | |
| 8,157,730 B2 | 4/2012 | Tucker et al. | |
| 8,222,041 B2 | 7/2012 | Pearton et al. | |
| 8,244,355 B2 | 8/2012 | Bennett et al. | |
| 8,294,135 B2 | 10/2012 | Lebedev et al. | |
| 8,366,630 B2 | 2/2013 | Haick et al. | |
| 8,449,824 B2 * | 5/2013 | Sun ..................... | G01N 27/414 |
| | | | 436/63 |
| 8,479,731 B2 | 7/2013 | Heinonen et al. | |
| 8,481,324 B2 | 7/2013 | Nakhoul et al. | |
| 8,494,606 B2 | 7/2013 | Debreczeny et al. | |
| 8,529,459 B2 | 9/2013 | Stahl et al. | |
| 8,581,262 B2 | 11/2013 | Pan et al. | |
| 8,597,953 B2 | 12/2013 | Haick et al. | |
| 8,747,325 B2 | 6/2014 | Bacal et al. | |

| | | | |
|---|---|---|---|
| 8,828,713 B2 | 9/2014 | Ren et al. | |
| 8,835,984 B2 | 9/2014 | Ren et al. | |
| 8,848,189 B2 | 9/2014 | Goldshtein et al. | |
| 8,951,473 B2 | 2/2015 | Wang et al. | |
| 8,955,367 B2 | 2/2015 | Gouma et al. | |
| 8,961,830 B2 | 2/2015 | Reynolds et al. | |
| 9,011,779 B1 | 4/2015 | Anglin et al. | |
| 9,029,168 B2 | 5/2015 | Mannoor et al. | |
| 9,034,170 B2 | 5/2015 | Blackburn et al. | |
| 9,085,715 B2 | 7/2015 | Berthelot et al. | |
| 9,103,775 B2 | 8/2015 | Bradley et al. | |
| 9,138,169 B2 | 9/2015 | Beard | |
| 9,147,398 B2 | 9/2015 | White et al. | |
| 9,147,851 B1 | 9/2015 | Bartsch et al. | |
| 9,267,908 B2 | 2/2016 | Wang et al. | |
| 9,299,238 B1 | 3/2016 | Ahmad et al. | |
| 9,315,848 B2 | 4/2016 | Haick et al. | |
| 9,316,637 B2 | 4/2016 | Ren et al. | |
| 9,324,825 B2 | 4/2016 | Ravesi et al. | |
| 9,366,664 B2 | 6/2016 | Anglin et al. | |
| 9,410,040 B2 | 8/2016 | Li et al. | |
| 9,513,244 B2 | 12/2016 | Koester | |
| 9,528,979 B2 | 12/2016 | Haick et al. | |
| 9,618,476 B2 | 4/2017 | Goldsmith | |
| 9,638,169 B2 | 5/2017 | Obrecht | |
| 9,642,577 B1 | 5/2017 | Li et al. | |
| 9,671,392 B2 | 6/2017 | Jeppsen et al. | |
| 9,689,836 B2 | 6/2017 | Makaram et al. | |
| 9,696,311 B2 | 7/2017 | Haick et al. | |
| 9,763,600 B2 | 9/2017 | Van Kesteren et al. | |
| 9,765,395 B2 | 9/2017 | Goldsmith | |
| 9,775,241 B2 | 9/2017 | Walczak et al. | |
| 9,859,034 B2 | 1/2018 | Sjong | |
| 9,936,897 B2 | 4/2018 | Carlson et al. | |
| 9,977,011 B2 | 5/2018 | Beck et al. | |
| 10,034,621 B2 | 7/2018 | Wondka et al. | |
| 10,046,323 B2 | 8/2018 | Bos | |
| 10,307,080 B2 | 6/2019 | Ssenyange et al. | |
| 10,493,276 B2 | 12/2019 | Moffitt et al. | |
| 10,543,035 B2 | 1/2020 | Sutermeister et al. | |
| 10,545,090 B2 | 1/2020 | Karlsson | |
| 10,770,182 B2 | 9/2020 | Sherwood et al. | |
| 10,852,264 B2 | 12/2020 | Kelly et al. | |
| 11,079,371 B2 | 8/2021 | Zhen et al. | |
| 11,085,921 B2 | 8/2021 | Livache et al. | |
| 11,172,846 B2 | 11/2021 | Sherwood et al. | |
| 11,191,457 B2 | 12/2021 | Sherwood et al. | |
| 11,262,354 B2 | 3/2022 | Sherwood | |
| 11,662,325 B2 | 5/2023 | Sherwood et al. | |
| 11,714,058 B2 | 8/2023 | Kelly et al. | |
| 11,835,435 B2 | 12/2023 | Sherwood et al. | |
| 2002/0123749 A1 | 9/2002 | Jain et al. | |
| 2002/0142477 A1 | 10/2002 | Lewis et al. | |
| 2003/0051733 A1 | 3/2003 | Kotmel et al. | |
| 2003/0113713 A1 * | 6/2003 | Glezer ............... | G01N 33/5438 |
| | | | 435/5 |
| 2004/0039295 A1 | 2/2004 | Olbrich et al. | |
| 2004/0128088 A1 | 7/2004 | Laletin et al. | |
| 2006/0130557 A1 | 6/2006 | Leddy et al. | |
| 2006/0263255 A1 | 11/2006 | Han et al. | |
| 2006/0270940 A1 | 11/2006 | Tsukashima et al. | |
| 2007/0048181 A1 | 3/2007 | Chang et al. | |
| 2007/0083094 A1 | 4/2007 | Colburn et al. | |
| 2007/0167853 A1 | 7/2007 | Melker et al. | |
| 2007/0229818 A1 | 10/2007 | Duan et al. | |
| 2007/0265509 A1 | 11/2007 | Burch et al. | |
| 2008/0021339 A1 | 1/2008 | Gabriel et al. | |
| 2008/0038154 A1 | 2/2008 | Longbottom et al. | |
| 2008/0052122 A1 | 2/2008 | Iliff | |
| 2008/0146890 A1 | 6/2008 | LeBoeuf et al. | |
| 2008/0161709 A1 | 7/2008 | Bradley | |
| 2008/0183910 A1 | 7/2008 | Natoli et al. | |
| 2008/0228098 A1 | 9/2008 | Popov et al. | |
| 2008/0317636 A1 | 12/2008 | Brahim et al. | |
| 2009/0054799 A1 | 2/2009 | Vrtis et al. | |
| 2009/0104435 A1 | 4/2009 | Hutchison et al. | |
| 2009/0112115 A1 | 4/2009 | Huang et al. | |
| 2009/0230300 A1 | 9/2009 | Trevejo et al. | |
| 2010/0024533 A1 | 2/2010 | Kimura et al. | |

(56) References Cited

U.S. PATENT DOCUMENTS

| | | |
|---|---|---|
| 2010/0056892 A1 | 3/2010 | Ben-Barak et al. |
| 2010/0085067 A1 | 4/2010 | Gabriel et al. |
| 2010/0116021 A1 | 5/2010 | Obrien |
| 2010/0137733 A1 | 6/2010 | Wang et al. |
| 2010/0147303 A1 | 6/2010 | Jafari et al. |
| 2010/0188069 A1 | 7/2010 | Ren et al. |
| 2010/0198521 A1 | 8/2010 | Haick et al. |
| 2010/0216175 A1 | 8/2010 | Melker et al. |
| 2010/0268479 A1 | 10/2010 | Potyrailo et al. |
| 2010/0273665 A1 | 10/2010 | Haick et al. |
| 2011/0015872 A1 | 1/2011 | Haick et al. |
| 2011/0017587 A1 | 1/2011 | Zhamu et al. |
| 2011/0059476 A1 | 3/2011 | Shin et al. |
| 2011/0143962 A1 | 6/2011 | Chaubron et al. |
| 2011/0201956 A1 | 8/2011 | Alferness et al. |
| 2011/0269632 A1 | 11/2011 | Haick et al. |
| 2011/0283770 A1 | 11/2011 | Hok et al. |
| 2012/0100636 A1 | 4/2012 | Johal et al. |
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0245434 A1 | 9/2012 | Haick et al. |
| 2012/0245854 A1 | 9/2012 | Haick et al. |
| 2012/0277794 A1 | 11/2012 | Kountotsis et al. |
| 2012/0306802 A1 | 12/2012 | McCracken |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0100067 A1 | 4/2013 | Dews |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0165810 A1 | 6/2013 | Saatchi et al. |
| 2013/0171733 A1 | 7/2013 | Haick et al. |
| 2013/0178756 A1 | 7/2013 | Suzuki et al. |
| 2013/0211207 A1 | 8/2013 | Joseph et al. |
| 2013/0211852 A1 | 8/2013 | Roizen et al. |
| 2013/0224761 A1 | 8/2013 | Imberty et al. |
| 2013/0236981 A1 | 9/2013 | Haick et al. |
| 2013/0253358 A1 | 9/2013 | Phillips et al. |
| 2013/0267862 A1 | 10/2013 | Jaffe et al. |
| 2013/0289368 A1 | 10/2013 | Covington et al. |
| 2013/0306419 A1 | 11/2013 | Okuda |
| 2013/0331723 A1 | 12/2013 | Hernandez-Silveira et al. |
| 2013/0334579 A1 | 12/2013 | Accardi et al. |
| 2014/0018691 A1 | 1/2014 | McNeill et al. |
| 2014/0041436 A1 | 2/2014 | Knott et al. |
| 2014/0051956 A1 | 2/2014 | Dalene et al. |
| 2014/0094669 A1 | 4/2014 | Jaffe et al. |
| 2014/0122515 A1 | 5/2014 | Lee et al. |
| 2014/0145735 A1 | 5/2014 | Koester et al. |
| 2014/0171817 A1 | 6/2014 | Blanch et al. |
| 2014/0194703 A1 | 7/2014 | Wondka et al. |
| 2014/0275597 A1 | 9/2014 | Zhang et al. |
| 2014/0275854 A1 | 9/2014 | Venkatraman et al. |
| 2014/0276168 A1 | 9/2014 | Satya et al. |
| 2014/0294675 A1 | 10/2014 | Melker et al. |
| 2014/0318535 A1 | 10/2014 | Bullock et al. |
| 2014/0378790 A1 | 12/2014 | Cohen |
| 2015/0013429 A1 | 1/2015 | Atkin et al. |
| 2015/0017735 A1* | 1/2015 | Katta .................. G01N 29/022 |
| | | 436/151 |
| 2015/0031582 A1 | 1/2015 | Cai et al. |
| 2015/0038378 A1 | 2/2015 | Cheng et al. |
| 2015/0044710 A1 | 2/2015 | Dasgupta et al. |
| 2015/0064796 A1 | 3/2015 | Fu et al. |
| 2015/0065365 A1 | 3/2015 | Ahmad |
| 2015/0164373 A1 | 6/2015 | Davis et al. |
| 2015/0196251 A1 | 7/2015 | Outwater et al. |
| 2015/0250408 A1 | 9/2015 | Ssenyange et al. |

| | | |
|---|---|---|
| 2015/0257676 A1 | 9/2015 | Fries |
| 2015/0265184 A1 | 9/2015 | Wondka et al. |
| 2015/0289782 A1 | 10/2015 | Peverall et al. |
| 2015/0295562 A1 | 10/2015 | Agarwal et al. |
| 2015/0298115 A1 | 10/2015 | Campidelli et al. |
| 2015/0301021 A1 | 10/2015 | Haick et al. |
| 2015/0307936 A1 | 10/2015 | Goldsmith |
| 2015/0309018 A1 | 10/2015 | Goldsmith |
| 2015/0320338 A1 | 11/2015 | Kane et al. |
| 2015/0335266 A1 | 11/2015 | Cormier |
| 2015/0335267 A1 | 11/2015 | Cormier et al. |
| 2015/0338340 A1 | 11/2015 | Jiang et al. |
| 2015/0338390 A1 | 11/2015 | Anglin et al. |
| 2015/0351699 A1 | 12/2015 | Addison et al. |
| 2016/0025675 A1 | 1/2016 | Goldsmith |
| 2016/0054312 A1 | 2/2016 | Goldsmith |
| 2016/0089089 A1 | 3/2016 | Kakkar et al. |
| 2016/0093806 A1 | 3/2016 | Turchanin |
| 2016/0109440 A1* | 4/2016 | Sherwood ........ G01N 33/54366 |
| | | 436/501 |
| 2016/0116431 A1 | 4/2016 | Accardi et al. |
| 2016/0150995 A1 | 6/2016 | Ratto et al. |
| 2016/0157752 A1 | 6/2016 | Cho et al. |
| 2016/0192861 A1 | 7/2016 | Gedeon et al. |
| 2016/0231309 A1 | 8/2016 | Ahmad et al. |
| 2016/0289769 A1 | 10/2016 | Schwartz et al. |
| 2016/0334381 A1 | 11/2016 | King-Smith et al. |
| 2016/0334386 A1 | 11/2016 | Anglin et al. |
| 2016/0356741 A1 | 12/2016 | Makaram et al. |
| 2016/0370337 A1 | 12/2016 | Blackley |
| 2017/0014043 A1 | 1/2017 | McDonnell |
| 2017/0042435 A1 | 2/2017 | Vermeulen et al. |
| 2017/0053068 A1 | 2/2017 | Pillai et al. |
| 2017/0067888 A1 | 3/2017 | Taslim et al. |
| 2017/0082566 A1 | 3/2017 | Koester |
| 2017/0212116 A1 | 7/2017 | Braga et al. |
| 2017/0227491 A1 | 8/2017 | Johnson et al. |
| 2017/0248541 A1 | 8/2017 | Liu |
| 2017/0307562 A1 | 10/2017 | Goldsmith |
| 2017/0307576 A1 | 10/2017 | Anglin et al. |
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0035932 A1 | 2/2018 | Massova |
| 2018/0037952 A1 | 2/2018 | Goldsmith |
| 2018/0037985 A1 | 2/2018 | Myers et al. |
| 2018/0048008 A1 | 2/2018 | Johnston et al. |
| 2018/0110444 A1 | 4/2018 | Sherwood et al. |
| 2018/0328841 A1 | 11/2018 | Graham et al. |
| 2018/0336970 A1 | 11/2018 | Sherwood et al. |
| 2019/0025237 A1 | 1/2019 | Kelly et al. |
| 2019/0178837 A1 | 6/2019 | Xu et al. |
| 2019/0254538 A1 | 8/2019 | Erdman et al. |
| 2019/0257825 A1 | 8/2019 | Zhen et al. |
| 2019/0286866 A1 | 9/2019 | Gurt |
| 2019/0331661 A1 | 10/2019 | Zhen et al. |
| 2020/0166435 A1 | 5/2020 | Sherwood et al. |
| 2020/0191737 A1 | 6/2020 | Sherwood et al. |
| 2021/0057526 A1 | 2/2021 | Zhen et al. |
| 2021/0072208 A1 | 3/2021 | Sherwood et al. |
| 2021/0148848 A1 | 5/2021 | Kelly et al. |
| 2022/0334075 A1 | 10/2022 | Koester et al. |
| 2022/0365024 A1 | 11/2022 | Aran et al. |
| 2023/0393087 A1 | 12/2023 | Sherwood et al. |
| 2024/0255391 A1 | 8/2024 | Sherwood et al. |

FOREIGN PATENT DOCUMENTS

| | | |
|---|---|---|
| CN | 1301342 | 6/2001 |
| CN | 101209218 | 7/2008 |
| CN | 101685077 | 3/2010 |
| CN | 102183557 | 9/2011 |
| CN | 102770069 | 11/2012 |
| CN | 102941042 | 2/2013 |
| CN | 103332678 | 10/2013 |
| CN | 103814294 | 5/2014 |
| CN | 103950920 | 7/2014 |

(56)            References Cited

FOREIGN PATENT DOCUMENTS

| | | |
|---|---|---|
| CN | 103975237 | 8/2014 |
| CN | 104914138 | 9/2015 |
| CN | 103852505 | 11/2015 |
| CN | 103877574 | 1/2016 |
| CN | 105445335 | 3/2016 |
| CN | 105527321 | 4/2016 |
| CN | 105688995 | 6/2016 |
| CN | 106152924 | 11/2016 |
| CN | 106456986 | 2/2017 |
| CN | 106483184 | 3/2017 |
| CN | 106687174 | 5/2017 |
| CN | 107180706 | 9/2017 |
| CN | 108534887 | 9/2018 |
| CN | 109270130 | 1/2019 |
| CN | 109310326 | 2/2019 |
| CN | 109862829 | 6/2019 |
| CN | 110769742 | 2/2020 |
| CN | 107076693 | 9/2020 |
| CN | 111788477 | 10/2020 |
| CN | 112041672 | 12/2020 |
| CN | 113167758 | 7/2021 |
| CN | 113196047 | 7/2021 |
| EP | 1764153 | 3/2007 |
| EP | 1806414 | 7/2007 |
| EP | 2542921 | 1/2013 |
| EP | 3093653 | 11/2016 |
| EP | 3210007 | 8/2017 |
| EP | 3439544 | 2/2019 |
| EP | 3528703 | 8/2019 |
| EP | 3624678 | 3/2020 |
| EP | 3431977 | 12/2020 |
| EP | 3755995 | 12/2020 |
| EP | 3785025 | 3/2021 |
| EP | 3825683 | 5/2021 |
| EP | 3861329 | 8/2021 |
| EP | 3899515 | 10/2021 |
| IN | 201627028955 | 10/2016 |
| JP | H07507943 | 9/1995 |
| JP | H11174051 | 7/1999 |
| JP | 2002529694 | 9/2002 |
| JP | 2004081854 | 3/2004 |
| JP | 2005514081 | 5/2005 |
| JP | 2008516209 | 5/2008 |
| JP | 2009244074 | 10/2009 |
| JP | 2011102747 | 5/2011 |
| JP | 2011523363 | 8/2011 |
| JP | 2012122814 | 6/2012 |
| JP | 2012517276 | 8/2012 |
| JP | 2015508175 | 3/2015 |
| JP | 5837058 | 11/2015 |
| JP | 2016022415 | 2/2016 |
| JP | 2016511456 | 4/2016 |
| JP | 2016122249 | 7/2016 |
| JP | 2016154931 | 9/2016 |
| JP | 2017096927 | 6/2017 |
| JP | 2017123912 | 7/2017 |
| JP | 2019020415 | 2/2019 |
| JP | 2019527365 | 9/2019 |
| JP | 2019536013 | 12/2019 |
| JP | 2020521128 | 7/2020 |
| JP | 6868126 | 4/2021 |
| JP | 2021514478 | 6/2021 |
| KR | 20170057001 | 5/2017 |
| KR | 101797737 | 11/2017 |
| WO | WO9325142 | 12/1993 |
| WO | WO9947905 | 9/1999 |
| WO | WO2001070114 | 9/2001 |
| WO | WO2008083285 | 7/2008 |
| WO | WO2008088780 | 7/2008 |
| WO | WO2009020647 | 2/2009 |
| WO | WO2009135070 | 11/2009 |
| WO | WO2011109736 | 9/2011 |
| WO | WO2011158068 | 12/2011 |
| WO | 2012064704 | 5/2012 |
| WO | 2012127213 | 9/2012 |
| WO | WO2012135565 | 10/2012 |
| WO | WO2012138632 | 10/2012 |
| WO | WO2012145247 | 10/2012 |
| WO | 2013036839 | 3/2013 |
| WO | WO2013095730 | 6/2013 |
| WO | WO2013189502 | 12/2013 |
| WO | WO2014064740 | 5/2014 |
| WO | 2014143175 | 9/2014 |
| WO | WO2015134895 | 9/2015 |
| WO | WO2015179623 | 11/2015 |
| WO | WO2015191558 | 12/2015 |
| WO | 2016063148 | 4/2016 |
| WO | WO2016064740 | 4/2016 |
| WO | WO2016105464 | 6/2016 |
| WO | WO2016145300 | 9/2016 |
| WO | WO2017066583 | 4/2017 |
| WO | WO2017095922 | 6/2017 |
| WO | WO2017218464 | 12/2017 |
| WO | WO2018053932 | 3/2018 |
| WO | WO2018075731 | 4/2018 |
| WO | 2018215069 | 11/2018 |
| WO | WO2018213564 | 11/2018 |
| WO | WO2019164922 | 8/2019 |
| WO | WO2019209918 | 10/2019 |
| WO | 2020102880 | 5/2020 |
| WO | WO2020112825 | 6/2020 |
| WO | WO2020131567 | 6/2020 |
| WO | WO2021034844 | 2/2021 |
| WO | 2021222489 | 11/2021 |

OTHER PUBLICATIONS

"Non-Final Office Action," for U.S. Appl. No. 17/101,900 mailed Sep. 20, 2021 (48 pages).

"Notice of Allowance," for U.S. Appl. No. 14/883,895 mailed Oct. 22, 2021 (18 pages).

"Response to Communication Pursuant to Rules 161(1) and 162 EPC," for European Patent Application No. 19828373.1 filed Nov. 8, 2021 (22 pages).

"Response to Communication Pursuant to Rules 161(1) and 162 EPC," for European Patent Application No. 19836341.8 filed Jan. 7, 2022 (12 pages).

"Response to Communication Pursuant to Rules 70(2) and 70a(2)/ Rule 39(1)," for European Patent Application No. 20214733.6 filed Nov. 23, 2021 (4 pages).

"Response to Non-Final Rejection," mailed on Sep. 20, 2021 for U.S. Appl. No. 17/101,900, submitted via EFS-Web on Dec. 20, 2021, 10 pages.

"Second Office Action," for Chinese Patent Application No. 201780065376.2 mailed Nov. 16, 2021 (8 pages) with English Summary.

"Written Submission," in Response to Summons to Attend Oral Proceedings for European Patent Application No. 18731579.1 filed Nov. 30, 2021 (31 pages).

Groves, William A., et al. "Analysis of Solvent Vapors in Breath and Ambient Air with a Surface Acoustic Wave Sensor Array," Ann. Occup. Hyg., vol. 45, No. 8, pp. 609-623, 2001 (15 pages).

"First Office Action," for Chinese Patent Application No. 201980077885.6 mailed Aug. 30, 2023 (10 pages) with English Summary.

"International Preliminary Report on Patentability," for PCT Application No. PCT/US2022/025004 mailed Oct. 26, 2023 (11 pages).

"Summons to Attend Oral Proceedings," for European Patent Application No. 15790739.5 mailed Oct. 13, 2023 (8 pages).

File History for U.S. Appl. No. 14/883,895 downloaded Aug. 18, 2021 (526 pages).

File History for U.S. Appl. No. 15/621,103 downloaded Aug. 18, 2021 (682 pages).

File History for U.S. Appl. No. 15/787,985 downloaded Aug. 18, 2021 (494 pages).

File History for U.S. Appl. No. 15/982,506 downloaded Aug. 18, 2021 (281 pages).

File History for U.S. Appl. No. 16/037,218 downloaded Aug. 18, 2021 (278 pages).

(56) References Cited

OTHER PUBLICATIONS

File History for U.S. Appl. No. 16/280,635 downloaded Aug. 18, 2021 (353 pages).
File History for U.S. Appl. No. 16/393,177 downloaded Aug. 18, 2021 (358 pages).
File History for European Patent Application No. 15790739.5 downloaded Aug. 19, 2021 (238 pages).
File History for European Patent Application No. 18731579.1 downloaded Aug. 19, 2021 (283 pages).
File History for European Patent Application No. 18180455.0 downloaded Aug. 19, 2021 (351 pages).
"European Search Report," for Dutch Patent Application No. 2019492 dated Apr. 12, 2018 (10 pages).
"Extended European Search Report," for European Patent Application No. 20214733.6 mailed Apr. 21, 2021 (11 pages).
"FDC1004 4-Channel Capacitance-to-Digital Converter for Capacitive Sensing Solutions," Data Sheet SNOSCY5B Texas Instruments Aug. 2014—Revised 2015 (24 pages).
"FDC1004EVM User Guide," Literature No. SNAU163C, Texas Instruments August 2014—Revised Oct. 2016 (46 pages).
"First Examination Report," for Australian Patent Application No. 2019224011 mailed Apr. 9, 2021 (4 pages).
"First Office Action," for Chinese Patent Application No. 201580056417.2 mailed Feb. 11, 2019 (13 pages) with English summary.
"First Office Action," for Chinese Patent Application No. 201780030595.7 mailed Nov. 2, 2020 (12 pages) with English Summary.
"International Preliminary Report on Patentability," for PCT Application No. PCT/US2015/056243 mailed May 4, 2017 (8 pages).
"International Preliminary Report on Patentability," for PCT Application No. PCT/US2017/057318 mailed May 2, 2019 (11 pages).
"International Preliminary Report on Patentability," for PCT Application No. PCT/US2018/033166 mailed Nov. 28, 2019 (8 pages).
"International Preliminary Report on Patentability," for PCT Application No. PCT/US2018/037144 mailed Dec. 27, 2018 (7 pages).
"International Preliminary Report on Patentability," for PCT Application No. PCT/US2019/018741 mailed Sep. 3, 2020 (11 pages).
"International Preliminary Report on Patentability," for PCT Application No. PCT/US2019/028870 mailed Nov. 5, 2020 (11 pages).
"International Preliminary Report on Patentability," for PCT Application No. PCT/US2019/063324 mailed Jun. 10, 2021 (10 pages).
"International Preliminary Report on Patentability," for PCT Application No. PCT/US2019/065981 mailed Jul. 1, 2021 (8 pages).
"International Search Report and Written Opinion," for PCT Application No. PCT/US2015/056243, mailed Jan. 26, 2016 (12 pages).
"International Search Report and Written Opinion," for PCT Application No. PCT/US2017/037144 mailed Oct. 6, 2017 (11 pages).
"International Search Report and Written Opinion," for PCT Application No. PCT/US2017/057318 mailed Feb. 6, 2018 (14 pages).
"International Search Report and Written Opinion," for PCT Application No. PCT/US2018/033166 mailed Oct. 2, 2018 (12 pages).
"International Search Report and Written Opinion," for PCT Application No. PCT/US2019/018741 mailed May 6, 2019 (17 pages).
"International Search Report and Written Opinion," for PCT Application No. PCT/US2019/028870 mailed Aug. 20, 2019 (17 pages).
"International Search Report and Written Opinion," for PCT Application No. PCT/US2019/063324 mailed Mar. 27, 2020 (17 pages).
"International Search Report and Written Opinion," for PCT Application No. PCT/US2019/065981 mailed Mar. 16, 2020 (14 pages).
"International Search Report and Written Opinion," for PCT Application No. PCT/US2020/046829 mailed Nov. 18, 2020 (15 pages).
"International Search Report and Written Opinion," for PCT Application No. PCT/US2021/026778 mailed Aug. 3, 2021 (11 pages).
"Mechanical Data," DGS (S-PDSO-G10) DSC0010B Package Outline, Example Board Layout, and Stencil Design. Texas Instruments 2016 (5 pages).
"NANO Mobile Healthcare Inc.," Company Profile on Reuters.com URL <http://www.reuters.com/finance/stocks/companyProfile?symbol=VNTH.PK> accessed Mar. 17, 2017 (2 pages).
"Office Action," for Chinese Patent Application No. 201780065376.2 mailed Apr. 27, 2021 (10 pages) with English Summary.
"Office Action," for Japanese Patent Application No. 2019-517196 mailed Feb. 4, 2020 (10 pages) with English Translation.
"Office Action," for Japanese Patent Application No. 2019-520955 mailed Feb. 9, 2021 (11 pages) with English Translation.
"Office Action," for Japanese Patent Application No. 2019-520955 mailed Jul. 14, 2020 (10 pages) with English Translation.
"Office Action," for Japanese Patent Application No. 2019-563876 mailed Nov. 4, 2020 (5 pages) with English Summary.
"Package Materials Information," Tape and Reel Information and Box Dimensions. Texas Instruments Feb. 13, 2016 (2 pages).
"Package Option Addendum," Packaging Information for FDC1004DGSR, DGST, DSCJ, DSCR and DSCT Devices. Texas Instruments May 2015 (2 pages).
"Response to Communication Pursuant to Rules 161(1) and 162 EPC," for European Patent Application No. 17733246.7 filed May 29, 2019 (22 pages).
"Response to Communication Pursuant to Rules 161(1) and 162 EPC," for European Patent Application No. 17794832.0 filed Dec. 6, 2019 (9 pages).
"Response to Communication Pursuant to Rules 161(1) and 162 EPC," for European Patent Application No. 19709268.7 filed Apr. 1, 2021 (12 pages).
"Response to Communication Pursuant to Rules 161(1) and 162 EPC," for European Patent Application No. 19733177.0 filed Jun. 4, 2021 (20 pages).
"Response to Examination Report," for Australian Patent Application No. 2019224011 filed Jul. 23, 2021 (22 pages).
"Second Office Action," for Chinese Patent Application No. 201580056417.2 mailed Sep. 25, 2019 (8 pages) with English Summary.
"Second Office Action," for Chinese Patent Application No. 201780030595.7 mailed Jun. 17, 2021 (8 pages), with English Summary.
"Standard Terms and Conditions for Evaluation Modules," Texas Instruments 2016 (5 pages).
"Third Office Action," for Chinese Patent Application No. 201580056417.2 mailed Feb. 18, 2020 (9 pages) with English Summary.
Allen, Matthew J., et al."Honeycomb Carbon: A Review of Graphene," Chem. Rev. 2010, 110, 132-145 (14 pages).
An, Xiaohong, et al."Stable Aqueous Dispersions of Noncovalently Functionalized Graphene from Graphite and their Multifunctional High-Performance Applications," Nano Lett. 2010, 10, 4295-4301 (7 pages).
Arasaradnam, R. P., et al."Review Article: Next Generation Diagnostic Modalities in Gastroenterology—Gas Phase Volatile compound biomarker detection," Alimentary Pharmacology and Therapeutics 2014; 39: 780-789 (10 pages).
Bair, Kenneth W., et al."(1-Pyrenylmethyl)amino Alcohols, a New Class of Antitumor DNA intercalators. Discovery and Initial Amine Side Chain Structure-Activity Studies," J. Med. Chem. 1990, 33, 2385-2393 (9 pages).
Bard, Allen J., et al."Electrochemical Methods: Fundamentals and Applications," Wiley New York: 1980; vol. 2 (850 pages).
Bhadra, Sharmista, et al."Non-destructive detection of fish spoilage using a wireless basic volatile sensor," Talanta, vol. 134, Dec. 25, 2014 pp. 718-723 (6 pages).
Biedermann, Frank, et al."Experimental Binding Energies in Supramolecular Complexes," Chem. Rev. 2016, 116(9), 5216-5300 (85 pages).
Bock, Harald, et al."Helicenes from Diarylmaleimides," Organic Letters 2014, 16, 1546-1549 (5 pages).
Boeseken, J. "The Use of Boric Acid for the Determination of the Configuration of Carbohydrates," Adv. Carbohydr. Chem. 1949, 4, 189-210 (22 pages).
Boots, Agnes W., et al."The Versatile Use of Exhaled Volatile Organic Compounds in Human Health and Disease," J. Breath Res. 6 (2012) 027108 (21 pages).
Brust, Mathias, et al."Novel Gold-Dithiol Nano-Networks with Non-Metallic Electronic Properties," Adv. Mater. 1995, 7, No. 9 795-797 (3 pages).

(56)        References Cited

OTHER PUBLICATIONS

Brust, Mathias, et al."Synthesis of Thiol-derivatised Gold Nanoparticles in a Two-phase Liquid-Liquid System," J. Chem. Soc., Chem. Commun., 1994, 801-802 (2 pages).

Cao, Mengmei, et al."Electrochemical and Theoretical Study of π-π stacking Interactions between Graphitic Surfaces and Pyrene Derivatives," J. Phys. Chem. C 2014, 118(5), 2650-2659 (10 pages).

Capuano, Rosamaria, et al."Corroles-Porphyrins: A Teamwork for Gas Sensor Arrays," Sensors, 2015, vol. 15, pp. 8121-8130 (10 pages).

Chamberlain, Richard V. II, et al."Electrostatically-induced Inclusion of Anions in Cyclodextrin Monolayers on Electrodes," Langmuir 2000, 1388-1396 (9 pages).

Cheng, Zengguang, et al."Suspended Graphene Sensors with Improved Signal and Reduced Noise," Nano Lett. 2010, 10, 1864-1868 (5 pages).

Connors, Kenneth A., et al."The Stability of Cyclodextrin Complexes in Solution," Chem. Rev. 1997, 97, 1325-1357 (34 pages).

Deen, David A., et al."Graphene-Based Quantum Capacitance Wireless Vapor Sensors," IEEE Sensors Journal, vol. 14, No. 5, May 2014, pp. 1459-1466 (8 pages).

Di Natale, Corrado, et al."Lung Cancer Identification by the Analysis of Breath by Means of an Array of Non-Selective Gas Sensors," Biosensors and Bioelectronics 18 (2003) 1209-1218 (10 pages).

Droscher, S., et al."Quantum Capacitance and Density of States of Graphene," Phys. Scr. T146 (2012) 014009, pp. 1-5 (5 pages).

Ebrish, M. A., et al."Dielectric Thickness Dependence of Quantum Capacitance in Graphene Varactors with Local Metal Back Gates," Device Research Conference, 2012 (2 pages).

Ebrish, M. A., et al."Operation of Multi-Finger Graphene Quantum Capacitance Varactors using Planarized Local Bottom Gate Electrodes," Applied Physics Letters, vol. 100, No. 14, Apr. 2012 (4 pages).

Ebrish, Mona A., et al."Effect of Noncovalent Basal Plane Functionalization of the Quantum Capacitance in Graphene," ACS Appl. Mater. Interfaces 2014, 6, 10296-10303 (8 pages).

Elemans, Johannes A.A.W., et al."Molecular Materials by Self-Assembly of Porphyrins, Phthalocyanines, and Perylenes," Adv. Mater. 2006, 18, 1251-1266 (16 pages).

Fisher, James P., et al."Central Sympathetic Overactivity: Maladies and Mechanisms," Autonomic Neuroscience 148.1 (2009): 5-15 (11 pages).

Fogel, Yulia, et al."Graphitic Nanoribons with Dibenzo[e,l]pyrene Repeat Units: Synthesis and Self-Assembly," Macromolecules 2009, 42, 6878-6884 (7 pages).

Gautam, Madhav, et al."Gas sensing properites of graphene synthesized by chemical vapor deposition," Materials and Science Engineering C31 (2011) 1405-1411 (7 pages).

Georgakilas, Vasilios, et al."Functionalization of Graphene: Covalent and Non-Covalent Approaches, Derivatives and Applications," Chem. Rev. 2012, 112(11), 6156-6214 (59 pages).

Georgakilas, Vasilios, et al."Noncovalent Functionalization of Graphene and Graphene Oxide for Energy Materials, Biosensing, Catalytic, and Biomedical Applications," Chem. Rev. 2016, 116, 5464-5519 (56 pages).

Ghosh, Sujoy, et al."Effect of 1-Pyrene Carboxylic-Acid Functionalization of Graphene on Its Capacitive Energy Storage," J. Phys. Chem. C 2012, 116, 20688-20693 (6 pages).

Giancane, Gabriele, et al."State of Art in Porphyrin Langmuir-Blodgett Films as Chemical Sensors," Advances in Colloid and Interface Science, 2012, vol. 171-172, pp. 17-35 (Year: 2012), 19 pages.

Good, Robert J."Contact angle, wetting, and adhesion: a critical review," J. Adhesion Sci. Technol. 1992, vol. 6, No. 12, pp. 1269-1302 (34 pages).

Gorodetsky, Alon A., et al."Electrochemistry Using Self-assembled DNA Monolayers on Highly Oriented Pyrolytic Graphite," Langmuir 2006, 22, 7917-7922 (6 pages).

Guo, Yujing, et al."Cyclodextrin Functionalized Graphene Nanosheets with High Supramolecular Recognition Capability: synthesis and Host-Guest Inclusion for Enhanced Electrochemical Performance," ACS Nano, 2010, abstract only (2 pages).

Guo, Zanru, et al."Light-Switchable Single-Walled Carbon Nanotubes Based on Host-Guest Chemistry," Adv. Funct. Mater. 2013, 23, 5010-5018 (18 pages).

Hasobe, Taku "Photo- and Electro-Functional Self-Assembled Architectures of Porphyrins," Physics Chemistry Chemical Physics, 2012, 14, pp. 15975-15987 (Year: 2012), 13 pages.

Hill, Ernie W., et al. "Graphene Sensors," IEEE Sensors Journal, vol. 11, No. 12, Dec. 2011 (10 pages).

Hinnemo, Malkolm, et al."On Monolayer Formation of Pyrenebutyric Acid on Graphene," Langmuir, 2017, vol. 33, No. 14 pp. 3588-3593 (6 pages).

Hsiao, Min-Chien, et al."Preparation and properties of a graphene reinforced nanocomposite conducting plate," J. Mater. Chem., 2010, 20, 8496-8505 (10 pages).

Hsieh, Chien-Te, et al."Field emission from various CuO nanostructures," Applied Physics Letters 2003, vol. 83, No. 6 (3 pages).

Hu, Yuhai, et al."Chemically Functionalized Graphene and Their Applications in Electrochemical Energy Conversion and Storage," Advances in Graphene Science, Chapter 7, 2013, pp. 161-190 (30 pages).

Huang, Ke-Jing, et al."Novel electrochemical sensor based on functionalized graphene for simultaneous determination of adenine and guanine in DNA," Colloids and Surfaces B: Biointerfaces 82 (2011) 543-549 (7 pages).

Hunter, Christopher A., et al."The Nature of π-π Interactions," J. Am. Chem. Soc. 1990, 112, 5525-5534 (10 pages).

Iezhokin, I., et al."Porphyrin molecules boost the sensitivity of epitaxial graphene for NH3 detection," J. Phy.: Condens. Matter 29 (2017) (11 pages).

Jiao, Dezhi, et al."Supramolecular Peptide Amphiphile Vesicles through Host-Guest Complexation," Angew. Chem. Int. Ed. 2012, 51, 9633-9637 (5 pages).

Josef, Szejtli "Introduction and General Overview of Cyclodextrin Chemistry," Chem. Rev. 1998, 98, 1743-1753 (12 pages).

Kang, Xinhuang, et al."Glucose Oxidase-graphene-chitosan modified electrode for direct electrochemistry and glucose sensing," Biosensors and Bioelectronics 25 (2009) 901-905 (5 pages).

Koester, Steven J."High Quality Factor Graphene Varactors for Wireless Sensing Applications," Applied Physics Letters 99, 163105 (2011), 3 pages.

Koester, Steven J."Using the Quantum Capacitance in Graphene to Enable Varactors for Passive Wireless Sensing Applications," 2011 IEEE Sensors Proceedings, pp. 994-997, 2011 (4 pages).

Kozbial, Andrew, et al."Study on the surface energy of graphene by contact angle measurement," Langmuir 2014, 30 (28), 8598-8606 (28 pages).

Kuila, Tapas, et al."Chemical functionalization of graphene and its applications," Progress in Materials Science 57 (2012) 1061-1105 (45 pages).

Lauffer, Peter, et al."Molecular and electronic structure of PTCDA on bilayer graphene on SiC(0001) studied with scanning tunnerling microscopy," Phys. Stat. Sol. (b) 2008, 245, No. 10, 2064-2067 (4 pages).

Lechner, Christoph, et al."Adhesive Forces Between Aromatic Molecules and Graphene," The Journal of Physical Chemistry C 2014, 118(36), 20970-20981 (12 pages).

Lecourt, Thomas, et al."Triisobutylaluminium and Diisobutylaluminium Hydride as Molecular Scalpels: The Regioselective Stripping of Perbenzylate Sugars and Cyclodextrins," Chem. Eur. J. 2004, 10, 2960-2971 (12 pages).

Li, Errui, et al."Aliphatic Aldehyde Detection and Adsorption by Nonporous Adaptive Pillar[4]arene[1]quinone Crystals with Vapochromic Behavior," ACS Applied Materials & Interfaces, 2018, 10, 23147-23153 (23 pages).

Li, Xiao, et al."Digital Health: Tracking Physiomes and Activity Using Wearable Biosensors Reveals Useful Health-Related Information," PLoS Biology 15.1 (2017): e2001402 (30 pages).

(56)        References Cited

OTHER PUBLICATIONS

Liu, Sophie F., et al."Single-walled Carbon Nanotube-Metalloporphyrin Chemiresistive Gas Sensor Arrays for Volatile Organic Compounds," Chemistry of Materials, vol. 27, No. 10 (2015) pp. 3560-3563 (5 pages).

Liu, Yuxin, et al."Biological and Chemical Sensors based on Graphene Materials," Chem. Soc. Rev. 2012, 41 (6), 2283-2307 (27 pages).

Loh, Kian Ping, et al."The Chemistry of Graphene," J. Mater. Chem., 2010, 20, 2277-2289 (13 pages).

Long, Brenda, et al. "Non-Covalent Functionalization of Graphene Using Self-Assembly of Alkane-Amines," Adv. Funct. Mater. 2012, 22, 717-725 (9 pages).

Lu, Chun-Hua, et al."A Graphene Platform for Sensing Biomolecules," Angew. Chem. Int. Ed. 2009, 48, 4785-4787 (3 pages).

Ma, Rui, et al."Acetone Sensing Using Graphene Quantum Capacitance Varactors," 2016 IEEE Sensors, Orlando, FL, 2016 (3 pages).

Machado, Roberto F., et al. "Detection of Lung Cancer by Sensor Array Analyses of Exhaled Breath," Am J Respir Crit Care Med, vol. 171, 1286-1291 (2005), 6 pages.

Mann, Jason A., et al. "Improving the Binding Characteristics of Tripodal Compounds on Single Layer Graphene," American Chemical Society 2013, vol. 7, No. 8, 7193-7199 (7 pages).

Manochehry, Sepehr, et al."Optical biosensors utilizing graphene and functional DNA molecules," J. Mater. Res. 2017, 32(15), 2973-2983 (11 pages).

Mao, Shun, et al. "Specific Protein Detection Using Thermally Reduced Graphene Oxide Sheet Decorated with Gold Nanoparticle-Antibody Conjugates," Adv. Mater. 2010, 22, 3521-3526 (6 pages).

Nag, Sanada, et al."Ultrasensitive QRS made by supramolecular assembly of functionalized cyclodextrins and graphene for the detection of lung cancer VOC biomarkers," Journals of Materials Chemistry B 2014, 2, pp. 6571-6579 (9 pages).

Nakhleh, Morad K., et al."Diagnosis and Classification of 17 Diseases from 1404 Subjects via Pattern Analysis of Exhaled Molecules," ACS Nano 2017, 11, 112-125 (14 pages).

Navaneethan, Udayakumar, et al."Volatile Organic Compounds in Bile Can Diagnose Malignant Biliary Strictures in the Setting of Pancreatic Cancer: A Preliminary Observation," Gastrointest Endosc. Dec. 2014;80(6):1038-45 (8 pages).

Ohno, Yasuhide, et al."Electrolyte-Gated Graphene Field-Effect Transistors for Detecting pH and Protein Adsorption," Nano Letters 2009, vol. 9, No. 9, 3318-3322 (5 pages).

Olson, Eric J., et al."Capacitive Sensing of Intercalated H2O Molecules Using Graphene," ACS Appl. Mater. Interfaces 2015, 7(46), 25804-25812 (29 pages).

Olson, Eric J., et al."Getting More out of a Job Plot: Determination of Reactant to Product Stoichiometry in Cases of Displacement Reactions and n:n Complex Formation," J. Org. Chem. 2011, 76, 8406-8412 (7 pages).

Oprea, A., et al."Integrated Temperature, Humidity and Gas Sensors on Flexible Substrates for Low-Power Applications," 007 IEEE Sensors, Atlanta, GA, 2007, pp. 158-161 (4 pages).

Pathipati, Srinivasa Rao, et al."Modulation of charge transport properties of reduced graphene oxide by submonolayer physisorption of an organic dye," Organic Electronics 14 (2013) 1787-1792 (6 pages).

Peng, Gang, et al. "Diagnosing lung cancer in exhaled breath using gold nanoparticles," Nature nanotechnology, 2009, 4(10), 669-673 (5 pages).

Peressi, Maria "Surface Functionalization of Graphene," Graphene Chemistry, John Wiley & Sons, Ltd:2013, pp. 233-253 (21 pages).

Planz, B., et al. "The role of urinary cytology for detection of bladder cancer," EJSO (2005) 21, 304-308 (5 pages).

Poulston, S., et al."Surface Oxidation and Reduction of CuO and Cu2O Studied Using XPS and XAES," Surface and Interface Analysis, vol. 24, 811-820 (10 pages).

Putta, Chandrababu, et al."Palladium Nanoparticles on Beta-Cyclodextrin Functionalised Graphene Nanosheets: a Supramolecular Based Heterogeneous Catalyst for C—C Coupling Reactions under Green Reaction Conditions," RSC Adv., 2015, 5, 6652-6660 (9 pages).

Ramakumar, Sanjay, et al."Comparison of Screening Methods in the Detection of Bladder Cancer," The Journal of Urology vol. 161, 388-394, Feb. 1999 (7 pages).

Rekharsky, Mikhail V., et al."Complexation Thermodynamics of Cyclodextrins," Chem. Rev. 1998, 98, 1875-1917 (44 pages).

Reuillard, B., et al."Non-covalent double functionalization of carbon nanotubes wiht a NADH oxidation Ru(II)-based molecular catalyst and a NAD-dependent glucose dehydrogenase," Chem. Commun. 2014, 50(79), 11731-11734 (5 pages).

Rodner, Marius, et al."Graphene Decorated with Iron Oxide Nanoparticles for Highly Sensitive Interaction with Volatile Organic Compounds," Sensors 2019, 19, 918-026 (9 pages).

Rojas, Maria T., et al."Supported Monolayers Containing Pre-formed Binding-Sites—Synthesis and Interfacial Binding-Properties of a Thiolated Beta-Cyclodextrin Derivative," J. Am. Chem. Soc. 1995, 117, 336-343 (8 pages).

Rushi, A.D., et al."Exercising Substituents in porphyrins for real time selective sensing of volatile organic compounds," Sensors and Actuators B: Chemical, vol. 257, 2018, pp. 389-397 (9 pages).

Schedin, F., et al."Detection of Individual Gas Molecules Adsorbed on Graphene," Nat. Mater. 2007, 6(9), 652-655 (11 pages).

Shao, Yuyan "Graphene Based Electrochemical Sensor and Biosensors: A Review," Electroanalysis 2010, 22, No. 10, 1027-1036 (10 pages).

Shao, Yuyan, et al."Nitrogen-doped graphene and its electrochemical applications," J. Mater. Chem., 2010, 20, 7491-7496 (6 pages).

Song, Nan, et al."Applications of pillarenes, an emerging class of synthetic macrocycles," Science China Chemistry, 2014, 57(9), 1185-1198 (15 pages).

Swanson, Emily, et al."Self Assembly of Monolayers on Grpahene with Pyrene and Cyclodextrin Derivatives," Research Poster. Elon University, LANDO program, Research Experience for Undergraduates Program of the National Science Foundation, Council of Undergraduate Research Experiences for Undergraduates symposium in Washington, D.C., Oct. 23-24, 2016 (1 page).

Terse-Thakoor Trupti, et al."Graphene based biosensors for healthcare," J. Mater. Res. 2017, 32(15), 2905-2929 (25 pages).

Tripathi, Kumud Malika, et al."Recent Advances in Engineered Graphene and Composites for Detection of Volatile Organic Compounds (VOCs) and Non-Invasive Diseases Diagnosis," Carbon 110 (2016)97-129 (34 pages).

Turkevich, John, et al."A study of the nucleation and growth processes in the synthesis of colloidal gold," Discuss. Faraday Soc., 1951, 11, 55-75 (23 pages).

Vincent, Mark A., et al."Accurate Prediction of Adsorption Energies on Graphene, Using a Dispersion-Corrected Semiempirical Method Including Solvation," J. Chem. Inf. Model. 2014, 54, 2225-2260 (6 pages).

Wang, David "FDC1004: Basics of Capacitive Sensing and Applications," Application Report SNOA927, Texas Instruments Dec. 2014 (12 pages).

Wang, Lihua "A novel [beta]-cyclodextrin Functionalized Reduced Graphene Oxide Electrochemical Sensor for Blood Glucose Detection," International Journal of Electrochemical Science, Dec. 28, 2017 pp. 1594-1602 (9 pages).

Wang, Qing Hua, et al."Room-temperature molecular-resolution characterization of self-assembled organic monolayers on epitaxial graphene," Nature Chemistry 2009 vol. 1 (3), 206-211 (6 pages).

Wayu, Mulugeta B., et al."Electropolymerization of Beta-Cyclodextrin onto Multi-Walled Carbon Nanotube Composite Films for Enhanced Selective Detection of Uric Acid," Journal of Electroanalytical Chemistry 783 (2016), 192-200 (9 pages).

Xi, Yuxi, et al."Flexible Graphene Films via te Filtration of Water-Soluble Noncovalent Functionalized Graphene Sheets," J. Am. Chem. Soc. 2008, 130, 5856-5857 (2 pages).

Xu, Huifeng, et al."Direct Electrochemixtry and electrocatalysis of hemoglobin protein entrapped in graphene and chitosan composite film," Talanta 81 (2010) 334-338 (5 pages).

Yavari, Fazel, et al."Graphene-Based Chemical Sensors," J. Phys. Chem. Lett. 2012, 3, 1746-1753 (8 pages).

(56) References Cited

OTHER PUBLICATIONS

Zhang, Xu, et al."A Wide Measurement Range and Fast Update Rate Integrated Interface for Capacitive Sensors Array," IEEE Transactions on Circuits and Systems—1: Regular Papers, Vo. 61, No. 1, Jan. 2014, pp. 2-11 (10 pages).

Zhang, Yao, et al."Capacitive Sensing of Glucose in Electrolytes using Graphene Quantum Capacitance Varactors," ACS Appl. Mater. Interfaces 2017, 9, 38863-38869 (7 pages).

Zhang, Yao, et al."Glucose Sensing with Graphene Varactors," IEEE Sensors, Sensors 2016—Proceedings, Orlando, FL 2016 (3 pages).

Zhang, Yiheng, et al."Direct Measurements of the Interaction between Pyrene and Graphite in Aqueous Media by Single Molecule Force Spectroscopy: Understanding the π-π Interactions, " Langmuir 2007, 23, 7911-7915 (5 pages).

Zhao, Yan-Li, et al."Noncovalent Functionalization of Single-Walled Carbon Nanotubes," Accounts of Chemical Research 2009, vol. 42, No. 8. 1161-1171 (12 pages).

Zhen, Xue, et al."Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).

Zhu, Congzhi, et al."Mingling Electronic Chemical Sensors with Supramolecular Host-Guest Chemistry," Current Organic Chemistry, 2014, 18, 1957-1964 (8 pages).

Zhu, Yanwu, et al."Graphene and Graphene Oxide: Synthesis, Properties, and Applications," Adv. Mater. 2010, 22, 3906-3924 (19 pages).

"First Office Action," for Chinese Patent Application No. 201980082446.4 mailed Nov. 6, 2023 (11 pages) with English translation.

"Notice of Allowance," for U.S. Appl. No. 16/696,348 mailed Jul. 24, 2023 (11 pages).

"Response to Communication Pursuant to Article 94(3) EPC," for European Patent Application No. 20214733.6 filed May 23, 2023 (45 pages).

"Response to Non-Final Rejection," mailed on Mar. 24, 2023 for U.S. Appl. No. 16/696,348, submitted via EFS-Web on Jun. 22, 2023, 9 pages.

"Communication Pursuant to Article 94(3) EPC," for European Patent Application No. 17794832.0 mailed Mar. 16, 2023 (7 pages).

"Non-Final Office Action," for U.S. Appl. No. 16/696,348 mailed Mar. 24, 2023 (22 pages).

"Notice of Allowance," for U.S. Appl. No. 17/101,900 mailed Feb. 28, 2023 (31 pages).

"Response to Final Rejection," mailed on Nov. 3, 2022, for U.S. Appl. No. 16/696,348 (Pdsd 442.0340USU1), submitted via EFS-Web on Mar. 3, 2023, 11 pages.

"Second Office Action," for Chinese Patent Application No. 201810782878.3 mailed Feb. 25, 2023 (4 pages) with English Summary.

Huang, Qing-An, et al ."LC Passive Wireless Sensors Toward a Wireless Sensing Platform: Status, Prospects, and Challenges," Journal of Microelectromechanical Systems, vol. 25, No. 5, Oct. 2016, https://ieeexplore.ieee.org/abstract/document/7558121 (20 pages).

"Communication Pursuant to Article 94(3) EPC," for European Patent Application No. 17733246.7 mailed Jan. 28, 2022 (6 pages).

"Communication Pursuant to Article 94(3) EPC," for European Patent Application No. 17794832.0 mailed Mar. 7, 2022 (9 pages).

"First Office Action," for Chinese Patent Application No. 201810782878.3 mailed Feb. 9, 2022 (14 pages) with English Summary.

"Non-Final Office Action," for U.S. Appl. No. 17/101,900 mailed Mar. 31, 2022 (16 pages).

"Office Action," for Japanese Patent Application No. 2018-133996 mailed Jan. 25, 2022 (7 pages) with English Translation.

"Communication Pursuant to Article 94(3) EPC," for European Patent Application No. 15790739.5 mailed Jun. 3, 2022 (5 pages).

"Decision of Rejection," for Chinese Patent Application No. 201780065376.2 mailed Apr. 1, 2022 (9 pages) with English Translation.

"Determination of Carbonyl Compounds By High performance Liquid Chromatography (HPLC)," EPA Method 8315A 1996 (34 pages).

"International Search Report and Written Opinion," for PCT Application No. PCT/US2022/025004 mailed Jul. 25, 2022 (15 pages).

"Non-Final Office Action," for U.S. Appl. No. 16/696,348 mailed Jun. 20, 2022 (68 pages).

"Non-Final Office Action," for U.S. Appl. No. 16/712,255 mailed Jun. 23, 2022 (64 pages).

"Office Action," for Japanese Patent Application No. 2018-133996 mailed Jul. 12, 2022 (4 pages) with English Translation.

"Response to Communication Pursuant to Article 94(3) EPC," for European Patent Application No. 17733246.7 filed May 18, 2022 (9 pages).

"Response to Communication Pursuant to Article 94(3) EPC," for European Patent Application No. 17794832.0 filed Jul. 7, 2022 (8 pages).

"Response to Non-Final Rejection," mailed on Jun. 20, 2022 for U.S. Appl. No. 16/696,348, submitted via EFS-Web on Sep. 20, 2022, 9 pages.

"Response to Non-Final Rejection," mailed on Jun. 23, 2022 for U.S. Appl. No. 16/712,255, submitted via EFS-Web on Sep. 22, 2022, 7 pages.

"Response to Non-Final Rejection," mailed on Mar. 31, 2022 for U.S. Appl. No. 17/101,900, submitted via EFS-Web on Jun. 28, 2022, 11 pages.

Agbonlahor, Osazuwa, et al."Adsorbed Molecules as Interchangeable Dopants and Scatterers with a van der Waals Bonding Memory in Graphene Sensors," ACS Sens. 2020, 5 (7), 2003-2009 (13 pages).

Bartosik, Miroslav, et al."The mechanism and suppression of physisorbed-water caused hysteresis in graphene FET sensors," ACS Sens., vol. 5, 2940-2949 (2020). (40 pages).

Cancilla, Devon A., et al."O-(2,3,4,5,6-Pentafluorophenyl)methylhydroxylamine hydrochloride: a versatile reagent for the determination of carbonyl-containing compounds," Journal of Chromatography, 627 (1992) 1-16 (16 pages).

Chen, Gugang, et al."Sub-ppt gas detection with pristine graphene," Applied Physics Letters 101, 053119 (2012) 6 pages.

Cui, Menghua, et al."Graphene-organic two-dimensional charge transfer complexes: inter-molecular electronic transitions and broadband near infrared photoresponse," J. Phys. Chem. C 2018, 122 (13), 7551-7556 (7 pages).

Dreyer, Daniel, et al."The chemistry of graphene oxide," Chem. Soc. Rev. 2010, 39(1), 228-240 (13 pages).

Fan, Xuge, et al. "Humidity and CO2 gas sensing properties of double-layer graphene," Carbon 127 (2018) 576-587 (12 pages).

Fuchs, Patricia, et al."Breath gas aldehydes as biomarkers of lung cancer," Int. J. Cancer 2010, 126 (11), 2663-70 (8 pages).

Gao, Zhaoli, et al."Scalable Production of Sensor Arrays Based on High-Mobility Hybrid Graphene Field Effect Transistors," ACS Applied Materials & Interfac. 2016, 8(41), 27546-27552 (8 pages).

Gavartin, J.L., et al."The role of nitrogen-related defects in high-k dialectric oxides: Density-functional studies.," Journal of Applied Physics. vol. 97, Issue 5. (15 pages).

Geim, A.K., et al."The rise of graphene," Nat. Mater. 2007, 6, 183-191 (9 pages).

Hayasaka, Takeshi, et al."The influences of temperature, humidity, and O2 on electrical properties of graphene FETs," Sensors & Actuators: B. Chemical 285 (2019) 116-122 (7 pages).

Hockstein, Neil G., et al."Diagnosis of Pneumonia with an Electronic Nose: Correlation of Vapor Signature with Chest Computed Tomography Scan Findings," The Laryngoscope 2004, 114 (10), 1701-1705 (5 pages).

Hong Chan, Wing, et al."Optodes based on a calixarene ester for the determination of aldehydes via in situ generation of the Girard's reagent P derivative," Analyst 1998, 123 (12), 2851-2856 (6 pages).

Hwang, Michael, et al."Ultrasensitive detection of nucleic acids using deformed graphene channel field effect biosensors," Nat. Commun. 2020, 11(1) (11 pages).

(56) References Cited

OTHER PUBLICATIONS

Ionescu, Radu, et al."Detection of Multiple Sclerosis from exhaled Breath Using Bilayers of Polycyclic Aromatic Hydrocarbons and Single-Wall Carbon Nanotubes," ACS Chemical Neurosci. 2011, 2(12), 687-693 (7 pages).

Kang, Junmo, et al. "Graphene Transfer: key for applications," Nanoscale, 2012, 4, 5527 (11 pages).

Knipp, Ralph J., et al."A versatile probe for chemoselective capture and analysis of carbonyl compounds in exhaled breath," Anal Methods, 2015, 7, 6027 (7 pages).

Kobayashi, Keiko, et al. "Gas chromatrographic determination of low-molecular-weight carbonyl compounds in aqueous solution as their O-(2,3,4,5,6-pentafluorobenzyl) oximes," Journal of Chromatography A 1980, 187(2), 413-417 (5 pages).

Li, Mingxiao, et al."Preconcentration and Analysis of Trace Volatile Carbonyl Compounds," Anal Chem 2012, 84(3), 1288-1293 (6 pages).

Lienerth, Peter, et al."Improving the Selectivity to Polar Vapors of OFET-Based Sensors by Using the Tranfser Charactersitics Hysteresis Response," Sensors and Actuators B 225 (2016) 90-95 (6 pages).

Liu, Yifei M., et al."Electrochemical Sensing of Nitric Oxide with Functionalized Graphene Electrodes," ACS Applied Materials & Interfaces 2013, 5(23), 12624-12630 (7 pages).

MacKin, Charles, et al. "Chemiresistive Graphene Sensors for Ammonia Detection," ACS Appl. Mater. Interfaces 2018, 10, 16169-16176 (8 pages).

Manolis, Antony "The Diagnostic Potential of Breath Analysis," Clin. Chem. 29/1, 5-15 (1983) (11 pages).

McCulloch, Michael, et al."Diagnostic Accuracy of Canine Scent Detection in Early-and Late-Stage Lung and Breast Cancers," Integrative Cancer Therapies 2006, 5(1), 30-39 (11 pages).

Moldoveanu, Serban C., et al."Derivatization Methods in GC and GC/MS," in Gas Chromatography-Derivatization, Sample Preparation, Application, Kusch, P., Ed. IntechOpen:2018 (33 pages).

Muruganathan, Manoharan, et al."Electrically Tunable van der Waals Interaction in Graphene—Molecule Complex," Nano Lett. 2015, 15(12), 8176-8180 (5 pages).

Novoselov, K.S., et al."Electric Field Effect in Atomically Thin Carbon Films," Science 2004, 306, 666-669 (5 pages).

Ou, Baoli, et al."Covalent functionalization of graphene with poly(methyl methacrylate) by atom transfer radical polymerization at room temperature," Polym. Chem., 2012, 3, 2768 (8 pages).

Park, Eun Uk, et al."Correlation between the sensitivity and the hysteresis of humidity sensors based on graphene oxides," Sensors and Actuators B 258 (2018) 255-262 (8 pages).

Poli, Diana, et al."Determination of aldehydes in exhaled breath of patients with lung cancer by means of on-fiber-derivatisation SPME-GC/MS," Journal of Chromatography B, 878 (2010) 2643-2651 (9 pages).

Pyo, Soonjae, et al."Improved photo- and chemical-responses of graphene via porphyrin-functionalization for flexible, transparent, and sensitive sensors," Nanotechnology 30 (2019) 215501 (9 pages).

Su, Qun, et al."Understanding Sources of Electrical Disorder in Graphene Grown by Chemical Vapor Deposition for Wafer-Scale Device Applications," ACS Appl. Nano Mater., vol. 2 (2019) 3426-3433 (26 pages).

Suk, Ji Won, et al."Transfer of CVD-Grown Monolayer Graphene onto Arbitrary Substrates," ACS Nano 2011, 5(9), 6916-6924 (10 pages).

Wei, Jinwei, et al."Understanding asymmetric transfer characteristics and hysteresis behaviors in graphene devices under different chemical atmospheres," Carbon 156 (2020) 67-76 (10 pages).

Wu, Ting, et al."Quantitative principles for precise engineering of sensitivity in carbon-based electrochemical sensors," Adv. Mater. 2018,1805752 (27 pages).

Xu, Mengjian, et al."Gate-polarity-dependent doping effects of H2O adsorption on graphene/SiO2 field-effect transistors," J. Phys. D: Appl. Phys. 53 455301, 2020, (8 pages).

Xu, Shicai, et al."Real-time reliable determination of binding kinetics of DNA hybridization using a multi-channel graphene biosensor," Nat. Commun. 2017, 8(1) 11 pages.

Yildiz, Ibrahim "A DFT Approach to the Mechanistic Study of Hydrozone Hydrolysis," J. Phys. Chem. A 2016, 120 (20), 3683-92 (25 pages).

Zheng, Peiru, et al. "Oxidation of graphene with variable defects: alternately symmetrical escape and self-restructuring of carbon rings," Nanoscale 2020, 12 (18), 10140-10148 (10 pages).

"Communication Pursuant to Article 94(3) EPC," for European Patent Application No. 20214733.6 mailed Jan. 16, 2023 (5 pages).

"Final Office Action, " for U.S. Appl. No. 16/696,348 mailed Nov. 3, 2022 (39 pages).

"International Preliminary Report on Patentability," for PCT Application No. PCT/US2021/026778 mailed Nov. 10, 2022 (7 pages).

"Non-Final Office Action," for U.S. Appl. No. 17/101,900 mailed Nov. 4, 2022 (19 pages).

"Notice of Allowance," for U.S. Appl. No. 16/712,255 mailed Jan. 20, 2023 (31 pages).

"Response to Communication Pursuant to Article 94(3) EPC," for European Patent Application No. 15790739.5 filed Oct. 12, 2022 (35 pages).

"Non-Final Office Action," for U.S. Appl. No. 17/719,760 mailed Jul. 11, 2024 (80 pages).

"Final Office Action," for U.S. Appl. No. 17/719,760 mailed Oct. 8, 2024 (22 pages).

"Non-Final Office Action," for U.S. Appl. No. 17/719,760 mailed Jan. 22, 2025 (22 pages).

"Non-Final Office Action," for U.S. Appl. No. 18/144,506 mailed Dec. 19, 2024 (66 pages).

"Response to Final Rejection," mailed on Oct. 8, 2024, for U.S. Appl. No. 17/719,760, submitted via EFS-Web on Jan. 8, 2025, 9 pages.

"Response to Non-Final Rejection," mailed on Jul. 11, 2024, for U.S. Appl. No. 17/719,760, submitted via Patent Center on Sep. 30, 2024, 8 pages.

"Non-Final Office Action," for U.S. Appl. No. 18/144,506 mailed May 30, 2025 (15 pages).

"Notice of Allowance," for U.S. Appl. No. 17/719,760 mailed Jul. 29, 2025 (11 pages).

"Response to Communication pursuant to Article 94(3)," for European Patent Application No. 22721582.9 filed Jul. 9, 2025 (10 pages).

"Response to Non-Final Rejection," mailed on Apr. 22, 2025, for U.S. Appl. No. 17/719,760, submitted via Patent Center on Jul. 14, 2025 (9 pages).

"Response to Non-Final Rejection," mailed on May 30, 2025, for U.S. Appl. No. 18/144,506, submitted via Patent Center on Aug. 26, 2025, 7 pages.

"Communication pursuant to Article 94(3)," for European Patent Application No. 22721582.9 mailed Mar. 17, 2025 (5 pages).

"Non-Final Office Action," for U.S. Appl. No. 17/719,760 mailed Apr. 22, 2025 (21 pages).

"Response to Non Final Office Action," for U.S. Appl. No. 18/144,506, filed on Mar. 12, 2025 (10 pages).

"Response to Non-Final Rejection," mailed on Jan. 22, 2025, for U.S. Appl. No. 17/719,760, submitted via Patent Center on Apr. 11, 2025, 7 pages.

Olson, Eric J., et al. "Capacitive Sensing of Intercalated H 2 O Molecules Using Graphene," Published date: 2015.

* cited by examiner

100

102 — Obtain a liquid biological sample from a subject

104 — Place the liquid biological sample into a container

106 — Contact the liquid biological sample with a first chemical sensor element having discrete graphene varactors 108 — Sense and store the capacitance of the discrete graphene varactors to obtain a sample data set

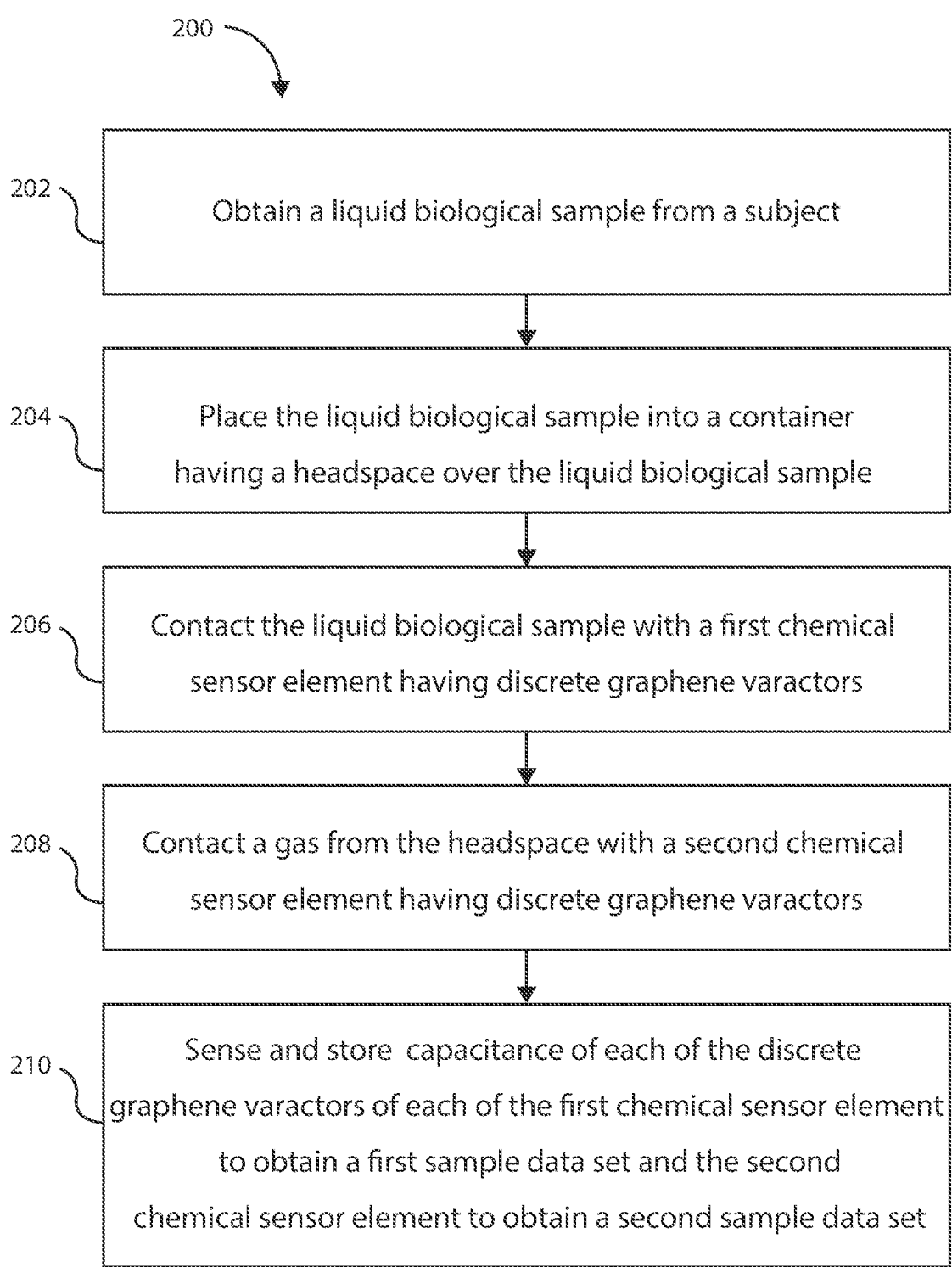

200

202  Obtain a liquid biological sample from a subject

204  Place the liquid biological sample into a container having a headspace over the liquid biological sample 206  Contact the liquid biological sample with a first chemical sensor element having discrete graphene varactors 208  Contact a gas from the headspace with a second chemical sensor element having discrete graphene varactors 210  Sense and store  capacitance of each of the discrete graphene varactors of each of the first chemical sensor element to obtain a first sample data set and the second chemical sensor element to obtain a second sample data set

NON-INVASIVE BLADDER CANCER DETECTION SYSTEM VIA LIQUID AND GASEOUS PHASE ANALYSIS

This application claims the benefit of U.S. Provisional Application No. 63/018,704, filed May 1, 2020, the content of which is herein incorporated by reference in its entirety.

FIELD

Embodiments herein relate to non-invasive bladder cancer detection systems and methods. More specifically, embodiments herein relate to non-invasive bladder cancer detection systems and methods for liquid and gaseous phase analysis.

BACKGROUND

According to the American Cancer Society bladder cancer accounts for approximately 80,000 new cancer cases each year. Bladder cancer can be classified into four stages, including stage I which can be characterized as affecting the level of the epithelium of the bladder wall; stage II which can be characterized as affecting the superficial muscle layer of the bladder wall as well as the epithelium; stage III which can be characterized as affecting the deep muscle layer of the bladder wall as well as the superficial muscle layer and the epithelium; and stage IV which can be characterized as being metastatic, affecting each of the layers of the bladder wall, any surrounding tissues and organs, or distant tissues and organs. If detected at stage I, bladder cancer survival rates can exceed 90%, and thus early detection methods are critical.

Current methods for detection of bladder cancer include those that are highly invasive or those that have low sensitivity and specificity. Invasive techniques such as cystoscopy can be extremely uncomfortable for a patient and can have a high risk of complications such as bleeding, pain, and infection. Cystoscopy is further limited as being less sensitive to stage I and stage II bladder cancer tumors, making early detection difficult. Less invasive techniques such as urine cytology tests utilize a patient's urine sample, but can have low sensitivity and specificity, and have high variability within different patient populations. Thus, a robust non-invasive, highly specific, and reproducible detection system is needed.

SUMMARY

In a first aspect, a method for detecting a disease state in a subject is included. The method includes obtaining a liquid biological sample from the subject and placing it into a container and contacting the liquid biological sample with a first chemical sensor element, where the first chemical sensor element can include a plurality of discrete graphene varactors. The method can include sensing and storing capacitance of each of the discrete graphene varactors to obtain a first sample data set.

In a second aspect, in addition to one or more of the preceding or following aspects, or in the alternative to some aspects, wherein obtaining a liquid biological sample includes obtaining one or more of a urine sample, a blood sample, a liquid suspension can include an organ biopsy sample, a sputum sample, a sweat sample, or a cell culture sample.

In a third aspect, in addition to one or more of the preceding or following aspects, or in the alternative to some aspects, the method further can include classifying the first sample data set into one or more preestablished disease states.

In a fourth aspect, in addition to one or more of the preceding or following aspects, or in the alternative to some aspects, the method further can include contacting a gas from a headspace surrounding the liquid biological sample with a second chemical sensor element can include a plurality of discrete graphene varactors.

In a fifth aspect, in addition to one or more of the preceding or following aspects, or in the alternative to some aspects, wherein the headspace surrounding the liquid biological sample includes a volume of a gas.

In a sixth aspect, in addition to one or more of the preceding or following aspects, or in the alternative to some aspects, the method further can include bubbling the liquid biological sample with a gas prior to contacting the gas from the headspace with a second chemical sensor element.

In a seventh aspect, in addition to one or more of the preceding or following aspects, or in the alternative to some aspects, wherein the container is flushed with an inert gas prior to placing the liquid biological sample into the container.

In an eighth aspect, in addition to one or more of the preceding or following aspects, or in the alternative to some aspects, wherein the liquid biological sample is contacted with the first chemical sensor element by submersing the first chemical sensor element into the liquid biological sample for a predetermined amount of time.

In a ninth aspect, in addition to one or more of the preceding or following aspects, or in the alternative to some aspects, wherein the liquid biological sample is contacted with the first chemical sensor element by capillary action of a fluid across the first chemical sensor element.

In a tenth aspect, in addition to one or more of the preceding or following aspects, or in the alternative to some aspects, wherein the liquid biological sample is incubated in the container for a period of time before the liquid biological sample is contacted with a chemical sensor element.

In an eleventh aspect, in addition to one or more of the preceding or following aspects, or in the alternative to some aspects, wherein sensing and storing capacitance of the discrete graphene varactors to obtain a sample data set is performed across a range of bias voltages, wherein the range of bias voltages is from $-3$ V to 3 V.

In a twelfth aspect, a method for detecting a disease state in a subject is included. The method can include obtaining a liquid biological sample from the subject and placing it into a container having a headspace above the liquid biological sample and contacting the liquid biological sample with a first chemical sensor element, where the first chemical sensor element can include a plurality of discrete graphene varactors. The method can include contacting a gas from the headspace above the liquid biological sample with a second chemical sensor element that includes a plurality of discrete graphene varactors. The method can include sensing and storing capacitance of each of the discrete graphene varactors of each of the first chemical sensor element to obtain a first sample data set and the second chemical sensor element to obtain a second sample data set.

In a thirteenth aspect, in addition to one or more of the preceding or following aspects, or in the alternative to some aspects, the method further can include classifying each of the first sample data set and the second sample data set into one or more preestablished disease states.

In a fourteenth aspect, in addition to one or more of the preceding or following aspects, or in the alternative to some aspects, wherein obtaining a liquid biological sample includes obtaining one or more of a urine sample, a blood sample, a liquid suspension can include an organ biopsy sample, a sputum sample, a sweat sample, or a cell culture sample.

In a fifteenth aspect, in addition to one or more of the preceding or following aspects, or in the alternative to some aspects, the method further including storing additional subject-specific data regarding the subject beyond sensed capacitance, the additional subject-specific data can include at least one of: prior disease states of the subject, age of the subject, results of a physical examination, symptoms experienced by the subject, current treatments received by the subject, prior treatments received by the subject, and prior data regarding specific biomarkers of one or more disease states.

In a sixteenth aspect, a system for detecting a disease state is included. The system can include a container, where the container can include a housing adapted to contain a liquid biological sample of a subject, the housing defining a headspace can include a volume of a gas. The system can include a first chemical sensor element configured to be contacted with the liquid biological sample, where the first chemical sensor element can include a plurality of discrete graphene varactors. The system can include a sensing device configured to interface with the first chemical sensor element, where the sensing device is further configured to sense a capacitance of the plurality of discrete graphene varactors.

In a seventeenth aspect, in addition to one or more of the preceding or following aspects, or in the alternative to some aspects, the system further can include a second chemical sensor element in fluid communication with the headspace, where the second chemical sensor element can include a plurality of discrete graphene varactors.

In an eighteenth aspect, in addition to one or more of the preceding or following aspects, or in the alternative to some aspects, the plurality of discrete graphene varactors each can include one or more surface modifications of a graphene surface.

In a nineteenth aspect, in addition to one or more of the preceding or following aspects, or in the alternative to some aspects, wherein the surface modifications of the plurality of discrete graphene varactors are configured to detect one or more biomarkers of a disease state, the biomarkers can include DNA, RNA, nucleolin, tumor cells, cell surface receptor proteins, C-reactive protein, transcription factors, cytokines, volatile organic compounds, exosomes, or derivatives and fragments thereof.

In a twentieth aspect, in addition to one or more of the preceding or following aspects, or in the alternative to some aspects, wherein the plurality of discrete graphene varactors are configured in an array.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 2 is a schematic flow diagram of an additional method for detecting a health condition in accordance with various embodiments herein.

Figure 1:
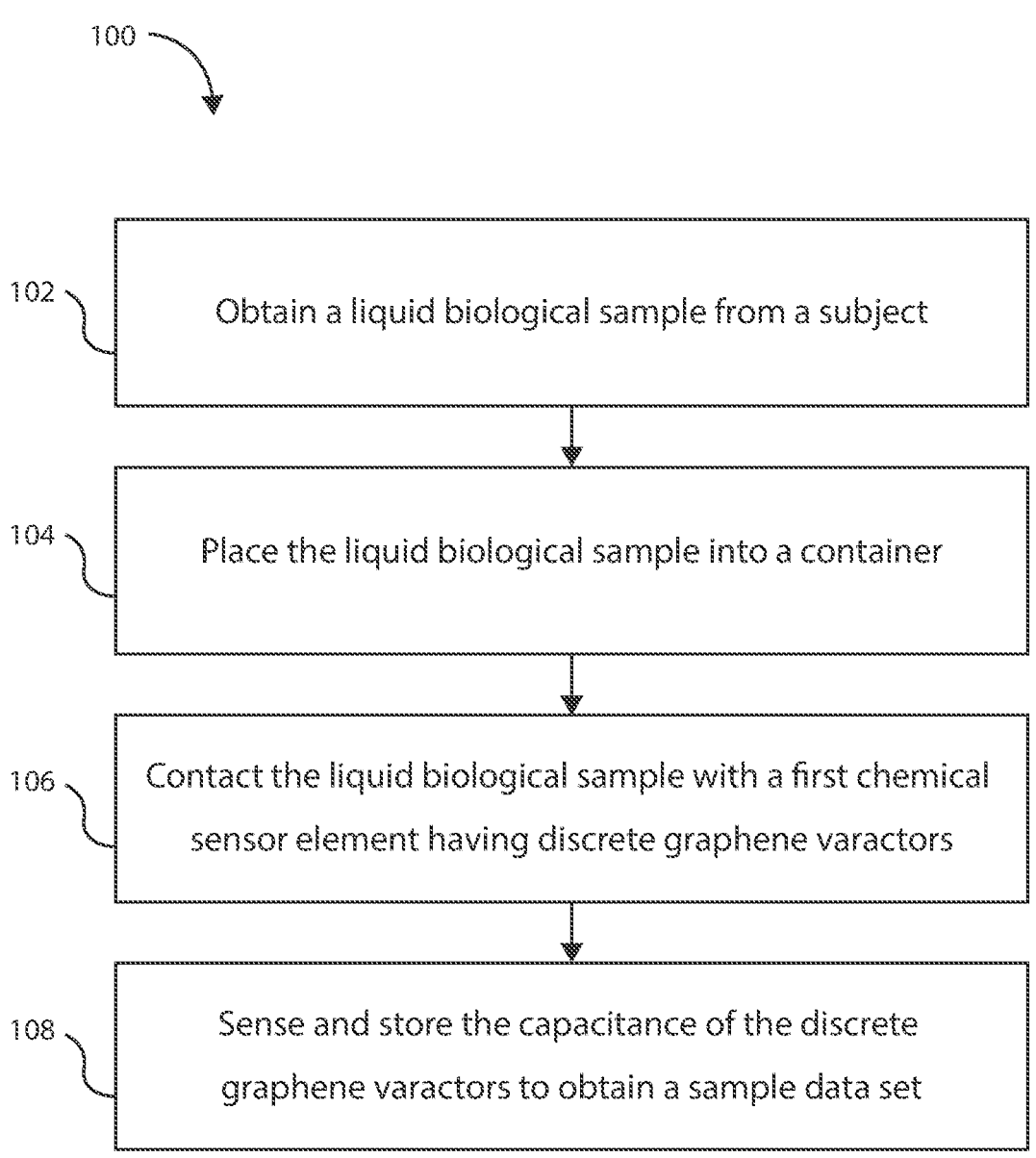
FIG. 1 is a schematic flow diagram of a method for detecting a health condition in accordance with various embodiments herein.

While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Bladder cancer can be detected based on a change in the metabolism of affected cells in the bladder. A change in cellular metabolism can result in the production of a number of urinary bladder cancer biomarkers found in the urine and blood. Such biomarkers can be found in the urine or blood as either soluble or insoluble molecules or can be released from both urine and blood as volatile organic compounds (VOCs). Detection of biomarkers within tissues, liquids, or solids obtained from a subject can be of substantial diagnostic value to help provide early detection, appropriate care, and/or treatment to a subject after onset of a disease state or other medical event, and can provide further benefit as a method for monitoring ongoing progress following treatment. In some cases, biomarkers released by cells in a disease state, and/or patterns of their release as compared to a healthy state, can be detected in small concentrations from a liquid biological sample of a subject.

A liquid biological sample from a patient can be placed in a container and biomarkers can be measured in both the gaseous and liquid phases. A discrete graphene varactor array can be exposed to the liquids held in the container or to gasses found within the headspace of the vessel and analyzed for a pattern of response specific to a particular health condition, such as a disease state. Typically, biomarkers associated with a healthy biological sample of a subject will have a different pattern of response from the discrete graphene varactor array as compared to biomarkers associated with a liquid biological sample from a disease state.

In accordance with embodiments herein, various biomarkers can be detected within a liquid biological sample of a subject to aid in the diagnosis of a disease state and/or as a part of methods of treating or caring for the same. In various embodiments, one or more biomarkers can be detected in a liquid biological sample of a subject where the liquid biological sample is of limited size. In other embodiments, analysis of biomarkers can be performed rapidly in the field, away from a care facility.

In some embodiments, detection of biomarkers and/or patterns related to the same for a period of time following onset of a disease can be used to monitor progress in response to a treatment or to alter a course of treatment as needed.

As used herein, the term "biomarkers" refers to a metabolite or analyte of a cell or population of cells. Various biomarkers can include, but are not to be limited to, biomarkers that are soluble in an aqueous medium, biomarkers that are insoluble in an aqueous medium, and volatile organic compounds (VOCs).

Referring now to FIG. 1, schematic view of a method 100 for detecting a disease state in a subject is shown in accordance with various embodiments herein. The method 100 can include obtaining a liquid biological sample from the subject at 102. The method 100 can include placing the liquid biological sample into a container at 104. The method 100 can include contacting the liquid biological sample with a first chemical sensor element at 106. The first chemical sensor element can include a plurality of discrete graphene varactors for sensing and storing capacitance of each of the discrete graphene varactors in response to binding by one or more biomarkers. The discrete graphene varactors will be discussed below in reference to FIGS. 18-22. The method 100 can include sensing and storing capacitance of each of the discrete graphene varactors to obtain a first sample data set at 108. In various embodiments herein, the method can include flushing a container with an inert gas such as nitrogen ($N_2$), helium (He), neon (Ne), argon (Ar), krypton (Kr), or xenon (Xe), prior to placing the liquid biological sample into the container. In some embodiments, the method 100 can further include classifying the first sample data set into one or more preestablished disease states, as will be discussed in more detail below. In various embodiments the subject is a human.

In some embodiments, obtaining a liquid biological sample can include obtaining one or more of a urine sample, a blood sample, a liquid suspension including an organ biopsy sample, a sputum sample, a sweat sample, or a cell culture sample. In some embodiments, obtaining a liquid biological sample from a subject can include obtaining a liquid biological sample immediately following the onset of a disease state or other medical event. The time points for obtaining a liquid biological sample can include, but are not be limited to, immediately after the onset of a disease state or other medical event, within 60 minutes following the onset of a disease state or other medical event, and within 1 day following the onset of a disease state or other medical event.

In some embodiments, obtaining a liquid biological sample from a subject can include obtaining a liquid biological sample one day following the onset of a disease state or other medical event, one week following the onset of a disease state or other medical event, two weeks following the onset of a disease state or other medical event, one month following the onset of a disease state or other medical event, six months following the onset of a disease state or other medical event, or one year following the onset of a disease state or other medical event. In other embodiments, obtaining a liquid biological sample from a subject can include obtaining a liquid biological sample more than one year following the onset of a disease state or other medical event. In some embodiments, obtaining a liquid biological sample from a subject can include obtaining a liquid biological sample at any of the foregoing times to monitor progression of a treatment for a disease state.

The liquid biological sample of a subject can be tested by contacting the liquid biological sample with one or more chemical sensor elements multiple times over a course of monitoring a subject for a health condition, such as a disease state. The liquid biological sample can be contacted with a first chemical sensor element by submersing the first chemical sensor element into the liquid biological sample for a predetermined amount of time. In some embodiments, the liquid biological sample can be contacted with the first chemical sensor element by capillary action of a fluid across the first chemical sensor element. In other embodiments, the liquid biological sample can be incubated in the container for a period of time before the liquid biological sample is contacted with a chemical sensor element.

The liquid biological sample can be obtained at various time points following the onset of a disease state or other medical event.

The obtained liquid biological sample of a subject can be tested at various time points following the onset of a disease state or other medical event, including immediately following obtaining a liquid biological sample, at 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 4 hours, 4.5 hours, 5 hours, 6 hours, 7 hours, 8 hours, 9 hours, 10 hours, 11 hours, 12 hours, 18 hours, 24 hours, 48 hours, or at various time points between any of the foregoing. In some embodiments, the liquid biological sample can be tested at greater than 48 hours. In other embodiments, the liquid biological sample can be tested only once at the time it was obtained.

Referring now to FIG. 2, a schematic view of a method 200 for detecting a disease state in a subject is shown in accordance with various embodiments herein. The method 200 can include obtaining a liquid biological sample from the subject at 202. The method 200 can include placing the liquid biological sample into a container having a headspace above the liquid biological sample at 204. The method 200 can include contacting the liquid biological sample with a first chemical sensor element at 206, where the first chemical sensor element can include a plurality of discrete graphene varactors. The method 200 can also include contacting a gas from the headspace above the liquid biological sample with a second chemical sensor element including a plurality of discrete graphene varactors at 208. The headspace surrounding the liquid biological sample can include a volume of a gas. The method 200 can also include sensing and storing capacitance of each of the discrete graphene varactors of the first chemical sensor element to obtain a first sample data set and of the second chemical sensor element to obtain a second sample data set at 210. In various embodiments, the method 200 can further include classifying the first sample data set and second sample data set into one or more preestablished disease states, as will be discussed in more detail below.

In various embodiments of the methods herein, the liquid biological sample can be bubbled with a gas prior to contacting the gas from the headspace with a second chemical sensor element. In some embodiments, the gas used to bubble the liquid biological sample can include an inert gas such as nitrogen ($N_2$), helium (He), neon (Ne), argon (Ar), krypton (Kr), or xenon (Xe). In other embodiments, the gas used to bubble the liquid biological sample can include ambient air or oxygen.

In some embodiments, the first sample data set and/or second sample data set can be analyzed to determine a disease state in a subject. In some embodiments, the first sample data set and second sample data set can be analyzed to determine an improvement or a worsening of a disease state of a subject over a period of time. In some embodiments, analyzing the first sample data set and second sample data set can include determining an improvement or a worsening of a disease state of a subject over 24 hours to 48 hours. In some embodiments, analyzing the first sample data set and second sample data set can include determining an improvement or a worsening of a disease state of a subject over 24 hours to 72 hours. In other embodiments, the method can include analyzing the first sample data set and second sample data set to determine an improvement or a worsening of a disease state of a subject over 1 week to 2 weeks or more. The first sample data set and second sample data set can be further analyzed to identify if the subject is a candidate for rehabilitation treatment, device therapy, interventional therapy, or drug therapy for the disease state.

In various embodiments, analyzing a first sample data set or second sample data set after sensing and storing capacitance of each of discrete graphene varactors to obtain a first sample data set or a second sample data set can be performed at multiple times following obtaining a liquid biological sample. In various embodiments, a first sample data set and a second sample data set can be analyzed immediately following obtaining a liquid biological sample. In some embodiments, a first sample data set and a second sample data set can be analyzed four hours following obtaining a liquid biological sample. In some embodiments, a first sample data set and a second sample data set can be analyzed eight hours following obtaining a liquid biological sample. In some embodiments, a first sample data set and a second sample data set can be analyzed 12 hours following obtaining a liquid biological sample. In some embodiments, a first sample data set and a second sample data set can be analyzed 16 hours following obtaining a liquid biological sample. In some embodiments, a first sample data set and a second sample data set can be analyzed 20 hours following obtaining a liquid biological sample. In some embodiments, a first sample data set and a second sample data set can be analyzed 24 hours following obtaining a liquid biological sample. In various embodiments, a first sample data set and a second sample data set can be analyzed multiple times over a 24-hour time after obtaining a liquid biological sample. It will be appreciated that multiple data sets can be analyzed, including a first sample data set, a second sample data set, a third data set, a fourth data set, a fifth data set, etc., at various time points following obtaining a liquid biological sample.

Sensing and storing capacitance of the graphene varactors to obtain a sample data set can be performed across a range of bias voltages. In some embodiments, the sensing and storing of capacitance of the graphene varactors can include sensing the capacitance from –3 V to 3 V. In some embodiments, the range of bias voltages can be from –2 V to 2 V. In other embodiments, the range of voltages can be from –1.5 V to 1.5 V. In some embodiments, the sensing of capacitance of the graphene varactors can include sensing the capacitance at –3 V, –2.5 V, –2.0 V, –1.5 V, –1.0 V, –0.5 V, 0.5 V, 1.0 V, 1.5 V, 2.0 V, 2.5 V, 3.0 V. It will be appreciated that the sensing and storing of capacitance of the graphene varactors can include sensing the capacitance within a range, wherein any of the foregoing voltages can serve as the lower or upper bound of the range, provided that the lower bound of the range is a value less than the upper bound of the range.

The sensing and storing of capacitance of the graphene varactors across a range of bias voltages can include sensing the capacitance in a stepped fashion. Sensing and storing of capacitance in a stepped fashion can be performed at voltage intervals, such as every 5 mV, 10 mV, 25 mV, 50 mV, 75 mV, 100 mV, 125 mV, 150 mV, 200 mV, 300 mV, 400 mV, or 500 mV, or by a stepped amount falling within a range between any of the foregoing.

When sensing and storing of capacitance of the graphene varactors across a range of bias voltages in a stepped fashion, a sample data set can be obtained at each bias voltage for each discrete graphene varactor. The sensing and storing of capacitance of the graphene varactors across a range of bias voltages to obtain a sample data set can include storing at least 10, 20, 30, 40, 50, 60, 70, 80, 90, 100, 125, 150, 175, 200, 250, 300, 350, 400, 450, 500, or more discrete capacitance values (or a number of discrete capacitance values falling within a range between any of the foregoing) for each graphene varactor across the range of bias voltages.

The methods herein can also include gathering and/or storing additional data regarding the subject beyond sensed capacitance as part of the sample data set that is classified.

In various embodiments, the methods can include storing additional subject-specific data regarding the subject beyond sensed capacitance. The additional subject-specific data can include, but not be limited to prior disease states of the subject; the time elapsed since a past disease state of the subject; age of the subject; results of one or more physical examinations; symptoms experienced by the subject; current treatments received by the subject; prior treatments received by the subject; and prior data regarding specific biomarkers of one or more disease states. The additional data can also include information regarding past treatment regimens, and successes or failures of past treatment regimens.

It will be appreciated that biomarkers in a liquid biological sample can interface with the discrete graphene varactors of the chemical sensor element to influence sensed capacitance. Biomarkers present in the liquid biological sample or biomarkers emitted as VOCs into a headspace can influence sensed capacitance. Biomarkers in a liquid biological sample of a subject in a disease state can be different (in terms of type, amount, etc.) than the biomarkers in a liquid biological sample of a subject in a non-disease state. One or more biological samples can be obtained from a subject during routine physical examination prior to the onset of a disease state or other medical event. The data obtained from sensing and storing capacitance from the liquid biological sample in a non-disease state can serve as a baseline value. Examples of obtaining a liquid biological sample in a non-disease state can include, but are not limited to, obtaining a liquid biological sample during a routine physical examination, obtaining a liquid biological sample prior to deployment for military duty, obtaining a liquid biological sample prior to undertaking an exercise or athletic regimen, or obtaining a liquid biological sample, on a daily, weekly, or monthly basis. In some embodiments, data from a liquid biological sample can be obtained from a subject in a clinical setting as part of a routine physical examination and can serve as a baseline for the biomarker content in that subject's liquid biological sample should disease occur at some point in the future.

Figure 3:
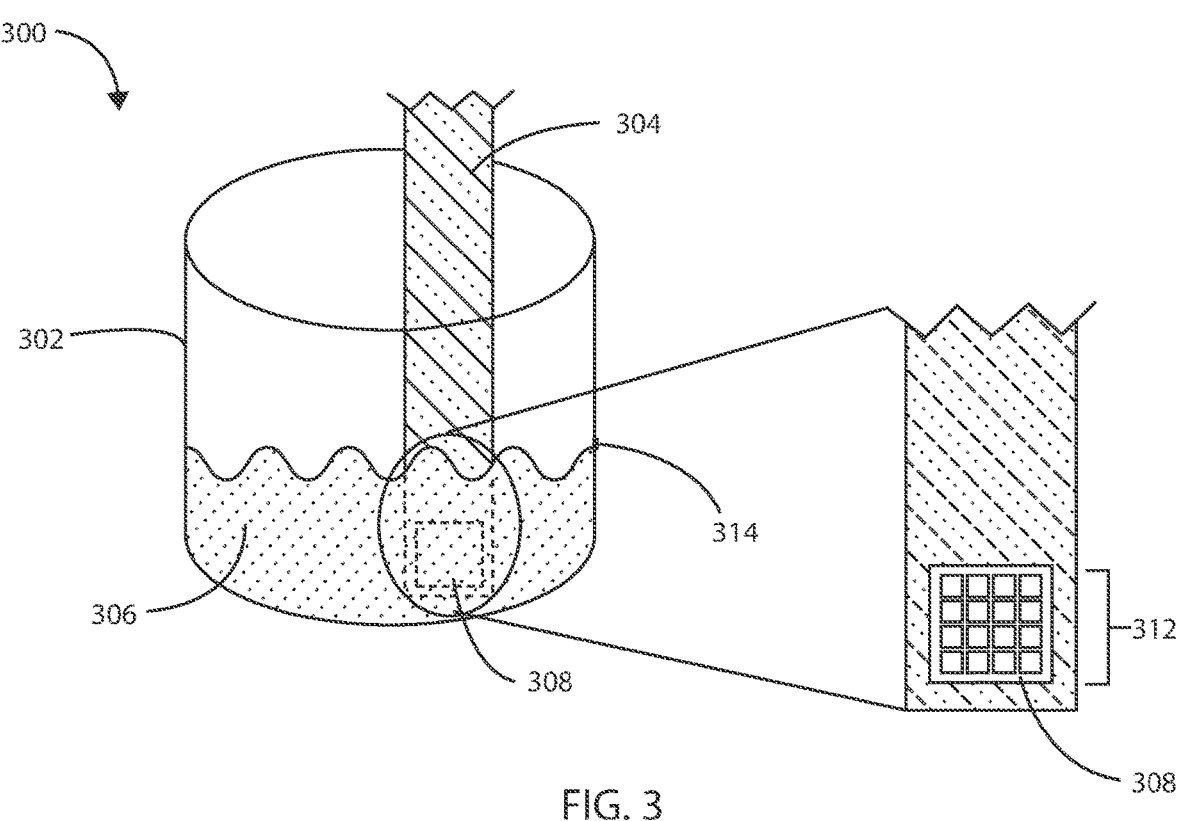
FIG. 3 is a schematic diagram of a container system in accordance with various embodiments herein.

Exemplary container systems suitable for use with the methods herein will be described in reference to FIGS. 3-14. Referring now to FIG. 3, a schematic diagram of a container system 300 for detecting a disease state is shown in accordance with various embodiments herein. Container system 300 can include a base housing 302 and a chemical sensor element probe 304. Chemical sensor element probe 304 can be in electrical communication with various components of the systems herein as will be discussed in reference to FIGS. 17-20. The base housing 302 can be adapted to contain a liquid biological sample 306 of a subject. The base housing can include a bottom wall and a cylindrical side wall, or a bottom wall and two, three, or four or more side walls. In various embodiments, the base housing 302 can include indicia 314, such as a scoring mark, raised metering line, inked line, etc. in order to indicate to a user a desired level for filling of a liquid biological sample into the container. While not depicted in FIG. 3, it will be appreciated that the container system 300 can further include a lid that can be removably attached to the base housing 302 so as to form a headspace within the container system 300, as will be discussed in more detail with respect to FIG. 5. As used herein, "headspace" can refer to a volume of gas above or surrounding a liquid biological sample 306. In various embodiments, the containers herein can be flushed with an inert gas prior to placing the liquid biological sample into the container.

Aspects of exemplary chemical sensor elements can be found in U.S. Patent Application Publication No. 2016/0109440A1, filed on Oct. 15, 2015, the content of which is herein incorporated by reference in its entirety.

It will be appreciated that in some embodiments, the chemical sensor element probe 304 can be placed in contact with a liquid biological sample 306. The chemical sensor element probe 304 can include a first chemical sensor element 308. The first chemical sensor element can include an array of discrete graphene varactors 312 for sensing and storing capacitance of each of the discrete graphene varactors in response to binding by one or more biomarkers. The discrete graphene varactors will be discussed in more detail below with respect to FIGS. 18-22. It will be appreciated that the chemical sensor elements herein that are used for contacting a liquid biological sample herein can be pre-treated to block non-specific biomarker binding by using a blocking agent such as bovine serum albumin (BSA), bovine serum, equine serum, rabbit serum, polyethylene glycol (PEG), casein, gelatin, polyvinylpyrrolidone (PVP), reconstituted milk powder (e.g., powdered cow's milk, powdered goat's milk), various surfactants, and the like.

In some embodiments the chemical sensor element probe 304 can be submersed in the liquid biological sample 306. In other embodiments, the liquid biological sample 306 can be added in a dropwise fashion to a surface of the chemical sensor element probe 304. In yet other embodiments, the liquid biological sample 306 can be a liquid biological sample stream and a surface of the chemical sensor element probe 304 can be placed into contact with a liquid biological sample stream. It will be appreciated that the first chemical sensor element 308 will be completely or partially submersed in the liquid biological sample 306 when the chemical sensor element probe 304 is placed in the liquid biological sample 306. While not shown in FIG. 3, it will be appreciated that container system 300 can include multiple chemical sensor element probes. It will further be appreciated that chemical sensor element probe 304 can include more than one chemical sensor element, to include a second chemical sensor element, a third chemical sensor element, a fourth chemical sensor element, and the like.

In various embodiments herein, the chemical sensor elements can be protected by an absorptive coating, film, or membrane that can absorb the liquid biological sample to allow transfer of a liquid biological sample to a surface of the chemical sensor element for analysis. In various other embodiments, the chemical sensor elements herein can include a protective cover on the surface of the chemical sensor element. A protective cover can include an epoxy, a ceramic, a metal, one or more polymers, or a mixture thereof.

The containers herein can be made from many materials, including glass, polymeric materials, metals, glasses, and the like. In some embodiments, the containers are sealed from the surrounding environment. In other embodiments the containers are open to the surrounding environment. In yet other embodiments, the containers are sterile on the interior.

The liquid biological sample volumes suitable for use with the containers herein can vary depending on the type and availability of the liquid biological sample. In some embodiments, the liquid biological sample volume can be from 1 microliter ($\mu$l) to about 1 milliliter (ml). In some embodiments, the liquid biological sample volume can be from 1 ml to 100 ml. In other embodiments, the liquid biological sample volume can be from 100 ml to 1 L. In various embodiments, the liquid biological sample volume can be 0.5 $\mu$l, 1 $\mu$l, 2 $\mu$l, 3 $\mu$l, 4 $\mu$l, 5 $\mu$l, 6 $\mu$l, 7 $\mu$l, 8 $\mu$l, 9 $\mu$l, 10 µl, 20 µl, 30 µl, 40 µl, 50 µl, 60 µl, 70 µl, 80 µl, 90 µl, 100 µl, 250 µl, 500 µl, 750 µl, 1 ml, 10 ml, 25 ml, 50 ml, 75 ml, 100 ml, 250 ml, 500 ml, 750 ml, or 1 L, or ranges bounded by one or more of these volumes. In yet other embodiments, the liquid biological sample volume can be greater than 1 L.

The total container volumes suitable for the containers herein can vary depending on the type and volume of the liquid biological sample. In some embodiments, the total container volume can be from 1 microliter (µl) to about milliliter (ml). In some embodiments, the total container volume can be from 1 ml to 100 ml. In other embodiments, the total container volume can be from 100 ml to 1 L. In various embodiments, the total container volume can be 1 µl, 2 µl, 3 µl, 4 µl, 5 µl, 6 µl, 7 µl, 8 µl, 9 µl, 10 µl, 20 µl, 30 µl, 40 µl, 50 µl, 60 µl, 70 µl, 80 µl, 90 µl, 100 µl, 250 µl, 500 µl, 750 µl, 1 ml, 10 ml, 25 ml, 50 ml, 75 ml, 100 ml, 250 ml, 500 ml, 750 ml, or 1 L. In yet other embodiments, the total container volume can be greater than 1 L, or ranges bounded by one or more of these volumes.

Figure 4:
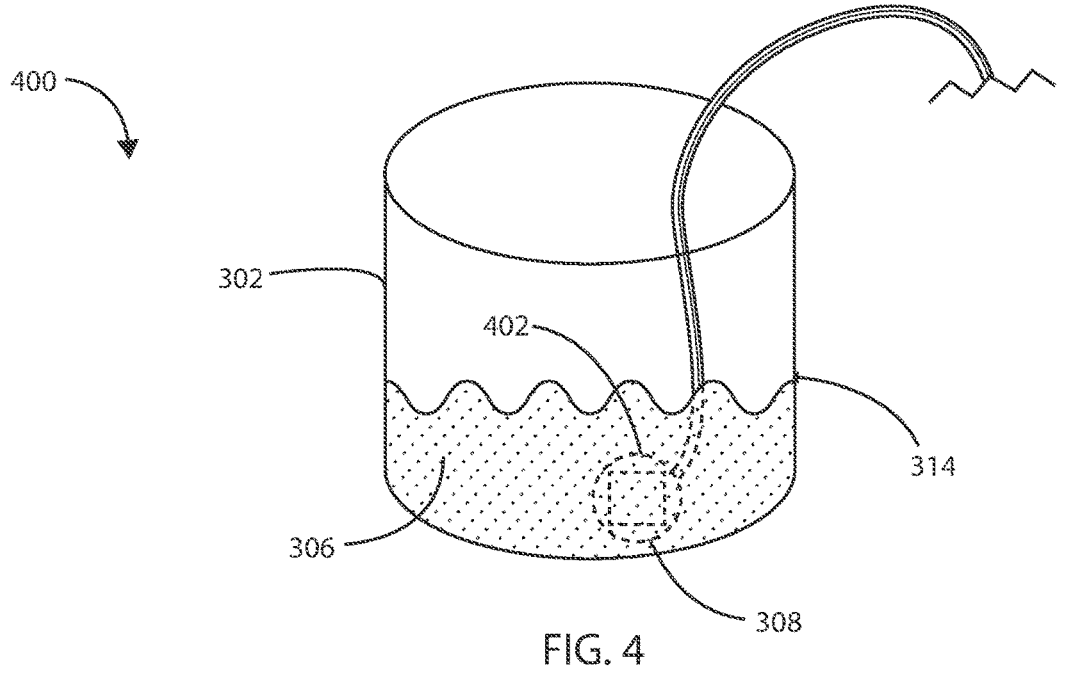
FIG. 4 is a schematic diagram of an additional embodiment of a container system in accordance with various embodiments herein.

Referring now to FIG. 4, a schematic diagram of a container system 400 for detecting a disease state is shown in accordance with various embodiments herein. Container system 400 can include a base housing 302 and a drop-in chemical sensor element ball 402. Drop-in chemical sensor element 402 can be in electrical communication with various components of the systems herein as will be discussed in reference to FIGS. 17-20. The base housing 302 can be adapted to contain a liquid biological sample 306 of a subject. In various embodiments, the base housing 302 can include indicia 314, such as a scoring mark, raised metering line, inked line, etc. in order to indicate to a user a desired level for filling of a liquid biological sample into the container. The drop-in chemical sensor element 402 can include a first chemical sensor element 308. While not shown in FIG. 4, it will be appreciated that drop-in chemical sensor element ball 402 can include more than one chemical sensor element, to include a second chemical sensor element, a third chemical sensor element, a fourth chemical sensor element, and the like.

Figure 5:
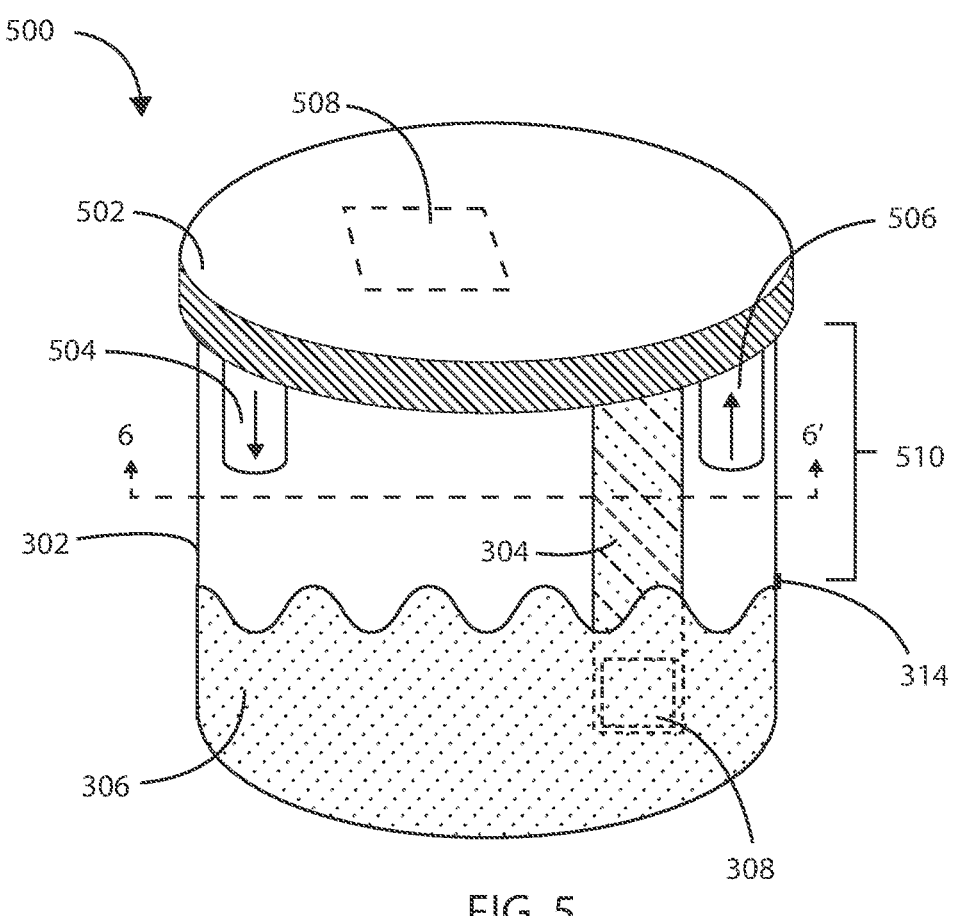
FIG. 5 is a schematic diagram of an additional embodiment of a container system in accordance with various embodiments herein.

In various embodiments, the containers herein can include a lid having a chemical sensor element exposed on an interior surface of the lid. Referring now to FIG. 5, a schematic diagram of a container system 500 for detecting a disease state is shown in accordance with various embodiments herein. Container system 500 can include a base housing 302 and lid 502. The lid 502 can be adapted to include a chemical sensor element probe 304. The lid 502 can further include a second chemical sensor element 508 configured to contact a headspace gas within container system 500 when the lid 502 is secured to a base housing 302. The base housing 302 can be adapted to contain a liquid biological sample 306 of a subject. In various embodiments, the base housing 302 can include indicia 314, such as a scoring mark, raised metering line, inked line, etc. in order to indicate to a user a desired level for filling of a liquid biological sample into the container, and can thus leave a headspace 510 volume within the container system 500 when the lid 502 is secured to a base housing 302. In various embodiments, container system 500 can include a fan to circulate a headspace gas in the vicinity of the chemical sensor element 508.

To optimize detection of VOCs emitted by a liquid biological sample, the headspace volume, the liquid biological sample volume, and the total volume of the container system can be tailored to the size and type of liquid biological sample. In some embodiments, the volume of the headspace can be from 0.5 volume percent (vol. %) of the total volume of the container system to about 15 vol. % of the total volume of the container system when a liquid biological sample is present. In other embodiments, the volume of the headspace can be from 10 vol. % to 50 vol. % of the total volume of the container system when a liquid biological sample is present. In yet other embodiments, the volume of the headspace can be from 75 vol. % to 95 vol. % of the total volume of the container system when a liquid biological sample is present. The volume of the headspace can be 0.5 vol. %, 1 vol. %, 2 vol. %, 3 vol. %, 4 vol. %, 5 vol. %, 6 vol. %, 7 vol. %, 8 vol. %, 9 vol. %, 10 vol. %, 15 vol. %, 20 vol. %, 25 vol. %, 30 vol. %, 35 vol. %, 40 vol. %, 45 vol. %, 50 vol. %, 55 vol. %, 60 vol. %, 65 vol. %, 70 vol. %, 75 vol. %, 80 vol. %, 85 vol. %, 90 vol. %, 95 vol. %, or 99 vol. % of the total container volume when a liquid biological sample is present. It will be appreciated that the volume of the headspace can include any volume percentage of the total volume of the container system within a range, wherein any of the foregoing volume percentages can serve as the lower or upper bound of the range, provided that the lower bound of the range is a value less than the upper bound of the range.

The headspace within a container system can also be customized with respect to the size of the liquid biological sample. For example, in some embodiments, the volume of the headspace can be 50% or less than the liquid biological sample volume. In some embodiments, the volume of the headspace can be 100% or less than the liquid biological sample volume. In other embodiments, the volume of the headspace can be 200% or less than the liquid biological sample volume. In yet other embodiments, the volume of the headspace can be 400% or less than the liquid biological sample volume.

The container system 500 can further include a gas inlet conduit 504 and a gas outlet conduit 506 defining a gas pathway to and from the headspace 510 along a surface of the second chemical sensor element 508. The gas pathway can be in fluid communication with the headspace 510 such that gas from within headspace 510 can diffuse through the gas pathway and to a surface of the second chemical sensor element 508. The lid 502 of container system 500 can be configured with the gas inlet conduit 504 and gas outlet conduit 506 such that the second chemical sensor element does not come into contact with any of the liquid biological sample 306.

Figure 6:
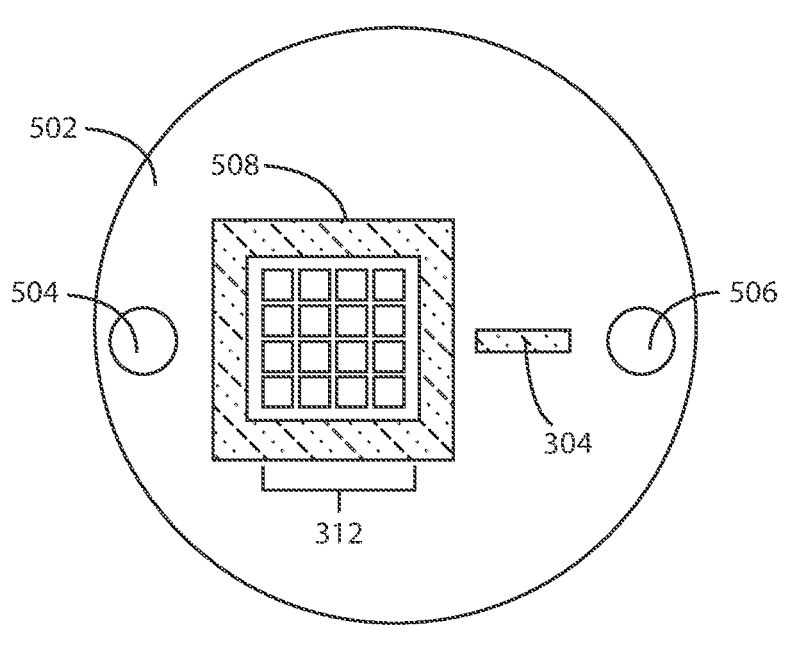
FIG. 6 is a schematic view of the container of FIG. 5 from line 6-6' in accordance with various embodiments herein.

A schematic view of the components of lid 502 as viewed looking toward an interior face of the container system 500 of FIG. 5 from line 6-6' is shown in FIG. 6. The lid 502 can include a gas inlet conduit 504 and a gas outlet conduit 506 defining a gas pathway to and from the headspace 510 along a surface of the second chemical sensor element 508. The second chemical sensor element can include an array of discrete graphene varactors 312 for sensing and storing capacitance of each of the discrete graphene varactors in response to binding by one or more biomarkers. The discrete graphene varactors will be discussed in more detail below with respect to FIGS. 18-22. The lid 502 can further include an integrated chemical sensor element probe 304 configured to be submersed into a liquid biological sample. It will be appreciated that in some embodiments, the lid 502 does not include an integrated chemical sensor element probe 304.

In various embodiments, the container systems herein can be configured for removal of an aliquot of the liquid biological sample for dispensing onto or into a separate chemical sensor element using various techniques including dispensing the liquid on the surface of a chemical sensor element; dispensing the liquid into via fluidization; dispensing the liquid via an aerosol, mist, or spray; or dispensing the liquid into via one or more droplets.

Figure 7:
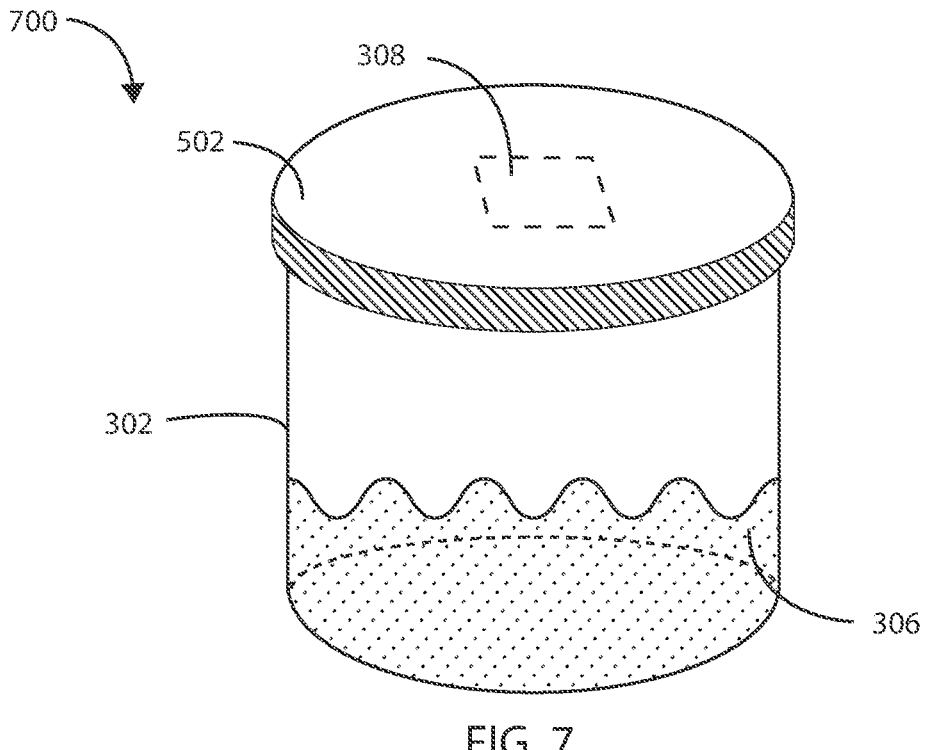
FIG. 7 is a schematic diagram of an additional embodiment of a container system in accordance with various embodiments herein.

In various embodiments, a chemical sensor element can be included as a part of either an interior surface of a lid or into an interior surface of a base housing, of the container systems herein. In various embodiments the chemical sensor element can be integrated into an interior surface of the lid or base housing, while in other embodiments a chemical sensor element can be affixed to an interior surface of a lid or base housing. Referring now to FIG. 7, a schematic diagram of a container system 700 for detecting a disease state is shown in accordance with various embodiments herein. Container system 700 can include a base housing 302 and a lid 502, where the lid 502 includes a first chemical sensor element 308 exposed on an interior surface the structure of the lid 502.

The base housing 302 of container system 700 can be adapted to contain a liquid biological sample 306 of a subject. The container system 700 can be used for moving, such as shaking or tipping a liquid biological sample 306 such that the liquid biological sample 306 comes into direct contact with the first chemical sensor element 308. It will be appreciated that the container system 700 can be so moved by a human hand or by mechanical means. The container system 700 can be so moved prior to sensing and storing capacitance of each of the discrete graphene varactors in response to binding by one or more biomarkers. In some embodiments, the container system 700 can be shaken during sensing and storing capacitance of each of the discrete graphene varactors in response to binding by one or more biomarkers.

In some embodiments, the liquid biological sample 306 can be shaken for from 5 seconds (sec) to 30 sec. In other embodiments, the time for shaking a liquid biological sample can be greater than or equal to 5 sec, 10 sec, 15 sec, 20 sec, 25 sec, 30 sec, 1.0 minutes (min), 1.5 min, 2.0 min, 2.5 min, 3.0 min, 3.5 min, 4.0 min, 4.5 min, or 5.0 min, or can be an amount falling within a range between any of the foregoing. In various embodiments, the liquid biological sample 306 can be shaken for more than 5 minutes.

Figure 8:
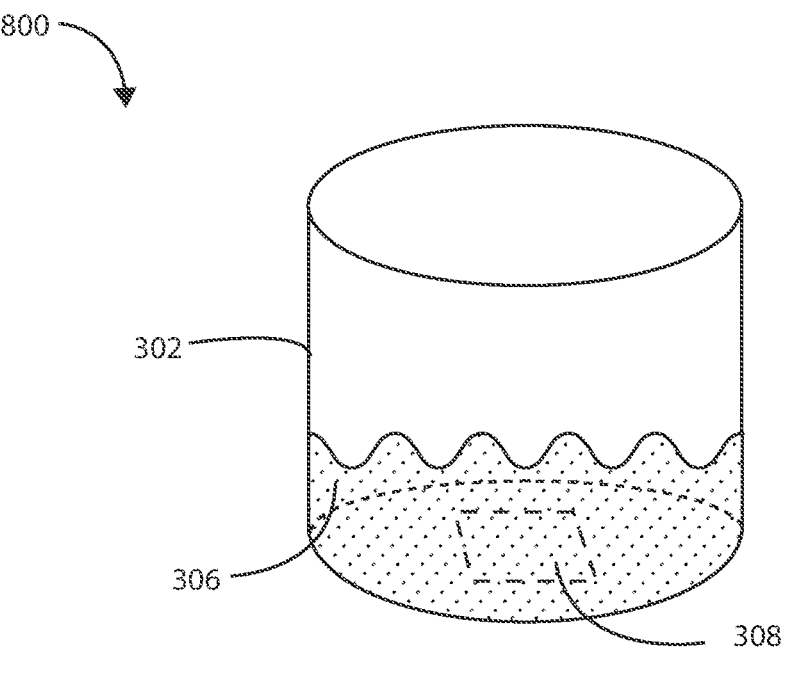
FIG. 8 is a schematic diagram of an additional embodiment of a container system in accordance with various embodiments herein.

Referring now to FIG. 8, a schematic diagram of a container system 800 for detecting a disease state is shown in accordance with various embodiments herein. Container system 800 can include a base housing 302 having a first chemical sensor element 308 as part of an interior surface the base housing 302, such as positioned on a bottom wall of the base housing 302. The base housing 302 can be adapted to contain a liquid biological sample 306 of a subject. The first chemical sensor element 308 can be configured to come into direct contact with the liquid biological sample 306. The liquid biological sample 306 can be held within the base housing 302 in direct contact with the first chemical sensor element 308 for a predetermined time prior to sensing and storing capacitance of each of the discrete graphene varactors in response to binding by one or more biomarkers. In various embodiments, the liquid biological sample can be held within the base housing of container system 800 from 5 sec, 10 sec, 15 sec, 20 sec, 25 sec, 30 sec, 1.0 min, 1.5 min, 2.0 min, 2.5 min, 3.0 min, 3.5 min, 4.0 min, 4.5 min, or 5.0 min, prior to sensing and storing capacitance of each of the discrete graphene varactors, or can be an amount falling within a range between any of the foregoing.

Figure 9:
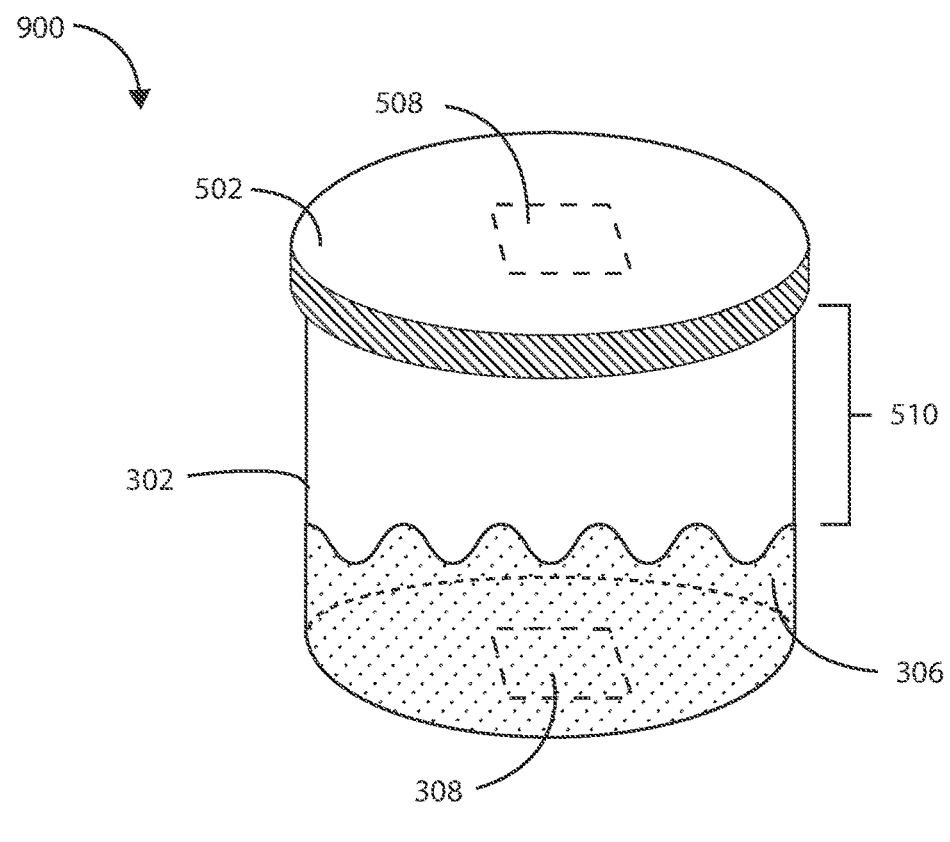
FIG. 9 is a schematic diagram of an additional embodiment of a container system in accordance with various embodiments herein.

The container systems herein can include a chemical sensor element as a part of both an interior surface of a lid and an interior surface of a base housing. Referring now to FIG. 9, a schematic diagram of a container system 900 for detecting a disease state is shown in accordance with various embodiments herein. Container system 900 can include a base housing 302 having a first chemical sensor element 308 as part of an interior surface the base housing 302, and a lid 502 having a second chemical sensor element 508 as part of an interior surface the structure of the lid 502. The base housing 302 can be adapted to contain a liquid biological sample 306 of a subject. The first chemical sensor element 308 can be configured to come into direct contact with the liquid biological sample 306. The second chemical sensor element 508 can be configured to come into direct contact with and to detect VOCs within a gas in the headspace 510 disposed over the liquid biological sample 306. It will be appreciated that the VOCs within a headspace 510 over the liquid biological sample 306 are released by the liquid biological sample 306.

Figure 10:
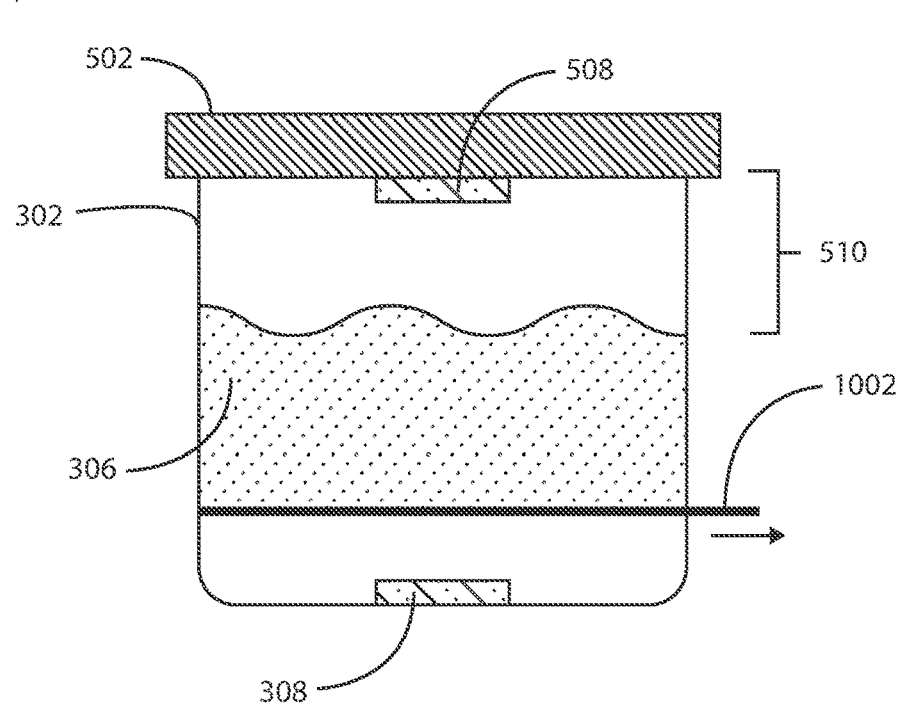
FIG. 10 is a schematic diagram of an additional embodiment of a container system in accordance with various embodiments herein.

It may be desirable to use a container system configured for delaying contacting a chemical sensor element with a liquid biological sample for a predetermined delay time. Referring now to FIG. 10, a schematic diagram of a container system 1000 for detecting a disease state is shown in accordance with various embodiments herein. Container system 1000 can include a base housing 302 having a first chemical sensor element 308 as part of an interior surface the base housing 302, and a lid 502 having a second chemical sensor element 508 as part of an interior surface the structure of the lid 502. The base housing 302 can be adapted to contain a liquid biological sample 306 of a subject. The container system 1000 can further include a movable partition 1002, such as a film, a foil, a movable wall, a sliding member, a mechanical iris, and the like, separating the liquid biological sample 306 from the first chemical sensor element 308. The first chemical sensor element 308 can be configured to come into direct contact with the liquid biological sample 306 after the movable partition 1002 has been moved enough to allow the liquid biological sample 306 into a volume defined by the movable partition 1002 and the base housing 302. The second chemical sensor element 508 can be configured to come into direct contact with and to detect VOCs within a gas in the headspace 510 disposed over the liquid biological sample 306.

The delay time for contacting a chemical sensor element with liquid biological sample obtained from a subject can include various time points following obtaining a liquid biological sample, including immediately following obtaining the liquid biological sample, at 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 4 hours, 4.5 hours, 5 hours, 6 hours, 7 hours, 8 hours, 9 hours, 10 hours, 11 hours, 12 hours, 18 hours, 24 hours, 48 hours, or at various time points between any of the foregoing. In some embodiments, the liquid biological sample can be tested at greater than 48 hours.

Figure 11:
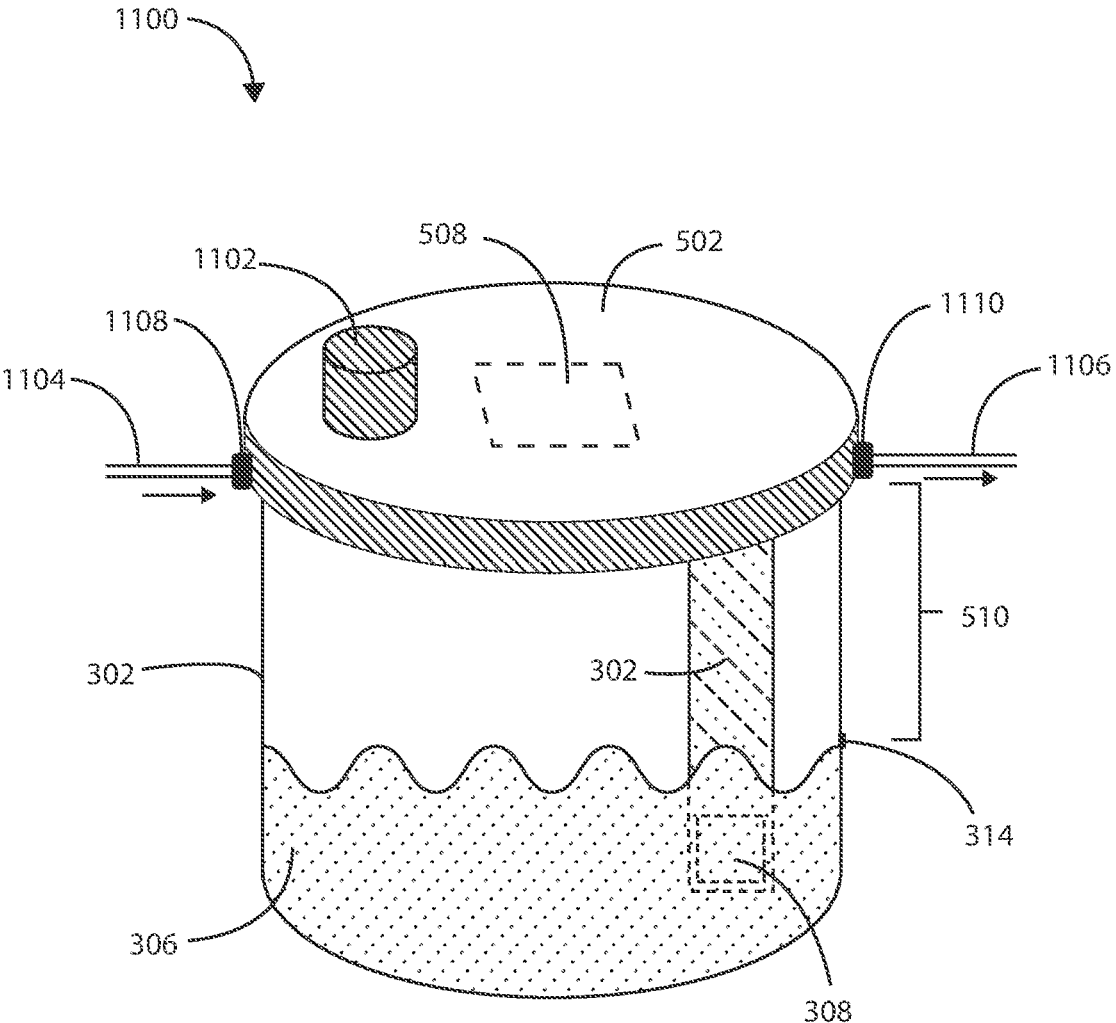
FIG. 11 is a schematic diagram of an additional embodiment of a container system in accordance with various embodiments herein.

Container systems herein can be placed under vacuum and can include a gas flow pathway that directs a headspace gas across a surface of a chemical sensor element on the lid of the container system. Referring now to FIG. 11, a schematic diagram of a container system 1100 is shown in accordance with various embodiments herein. Container system 1100 can include a base housing 302 to contain a liquid biological sample 306 of a subject. Container system 1100 can include a vacuum port 1102 for placing the container system 1100 under vacuum. The vacuum port 1102 can be removably connected to the container system 1100 or it can be integral with the container system 1100. In some embodiments, vacuum port 1102 can include a polymeric material that can be configured to receive a biopsy needle therethrough, such as a septum or a rubber stopper, for placing a liquid biological sample into the container. In some embodiments, the vacuum port 1102 can define an opening having a cap, lid, or other type of sealing mechanism.

In some embodiments the container can include a vacuum in the headspace prior to placing a liquid biological sample therein. In other embodiments, the container can include a partial vacuum in the headspace prior to placing a liquid biological sample therein. In some embodiments, the container can include a vacuum or partial vacuum. It will be appreciated that the pressure inside the vacuum can include any pressure that is lower than standard atmospheric pressure (i.e., less than 760 mm Hg). For example, in some embodiments the pressure can be lower than 760, 750, 740, 730, 720, 710, 700, 680, 660, 640, 620, 600, 580, 550, 500, 450, 400, 350, 300, 250, 200, 150, 100, or 50 mm Hg, or can fall within a range including any of the foregoing and can be so in a steady-state or transitorily. It will be appreciated that the pressure inside the vacuum can include any pressure that is lower than the ambient pressure of the environment surrounding the container. However, in other embodiments, the pressure within the container may be equal to or higher than the ambient pressure of the local environment. For example, in some embodiments the pressure can be higher than 760, 770, 800, 850, 900, 950, 1000, 1100, 1200, 1300, 1500, 1750, 2000, 2250, 2500, 2750, 3000, 3500, 4000, 5000, or 6000 mm Hg, or can fall within a range between any of the foregoing and can be so in a steady-state or transitorily.

The container system 1100 can include a gas inlet conduit 1104 and a gas outlet conduit 1106. Gas inlet conduit 1104 can be connected to a carrier gas supply line upstream from container system 1100. Gas from the headspace can be continuously drawn from the container system 1100 through gas outlet conduit 1106 to remove any VOCs present in the headspace and replenish the headspace gas with a gas that does not contain any VOCs. The carrier gas can include ambient air, or it can include an inert gas such as nitrogen (N$_2$), helium (He), neon (Ne), argon (Ar), krypton (Kr), or xenon (Xe). The carrier gas can be used to drive the gas within the headspace 510 out of the container through the gas outlet conduit 1106. The gas flow is depicted by the arrows in FIG. 11. The gas inlet conduit 1104 and gas outlet conduit 1106 can be integral to the container system 1100 or each can be connected to the container system 1100 by an airtight gasket, or gas inlet port 1108 and gas outlet port 1110.

In various embodiments, the carrier gas can be used to drive the gas within the headspace 510 out of the container through the gas outlet conduit 1106 and into contact with one or more chemical sensor elements downstream the container system 1100 (not shown). The gas flow is depicted by the arrows in FIG. 11. The gas inlet conduit 1104 and gas outlet conduit 1106 can be integral to the container system 1100 or each can be connected to the container system 1100 by an airtight gasket, or gas inlet port 1108 and gas outlet port 1110.

Figure 12:
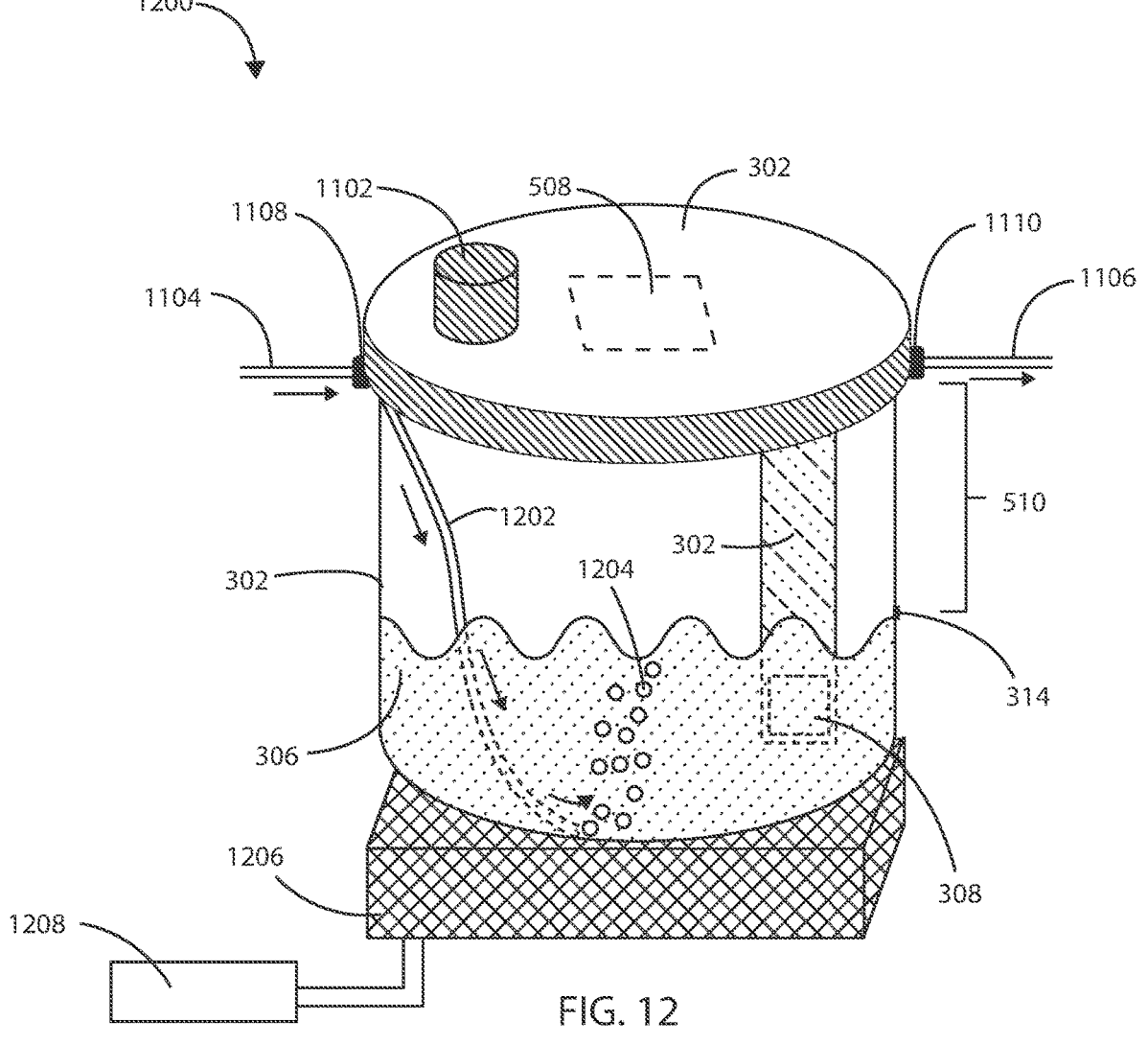
FIG. 12 is a schematic diagram of an additional embodiment of a container system in accordance with various embodiments herein.

In some embodiments, the liquid biological sample held within the container systems herein can bubbled with a carrier gas and/or can be heated using a temperature regulator. Referring now to FIG. 12, a schematic diagram of a container system 1200 is shown in accordance with various embodiments herein. The container system can include all features and elements of container system 1100, in addition to a bubbling gas conduit 1202 submerged within the liquid biological sample 306. The carrier gas 1204 bubbled through the liquid biological sample 306 can include ambient air, or it can include an inert gas such as nitrogen (N$_2$), helium (He), neon (Ne), argon (Ar), krypton (Kr), or xenon (Xe). The carrier gas can be bubbled through the liquid biological sample 306 to enhance or accelerate release of VOCs into the headspace 510.

In order to maintain the temperature of the liquid biological sample 306 at a desired temperature, such as within a physiological temperature range, a temperature regulator 1206 can be used. The container systems herein can be placed into contact with the temperature regulator such that the container system is either in direct contact or indirect contact with the temperature regulator 1206. In some embodiments, the temperature regulator 1206 can include a heat source that can be controlled by a thermostat 1208 that can be used to keep the temperature of the liquid biological sample constant. The temperature regulator 1206 can be used to increase or decrease the temperature of the liquid biological sample in a stepwise fashion. It will be appreciated that in some embodiments, the temperature regulator 1206 can alternatively include a cooling apparatus to remove heat and cool the temperature of the liquid biological sample below a desired temperature, such as below a physiological temperature range.

In some embodiments, liquid biological samples can be removed from a subject using a needle and syringe or cannula. To minimize handling of the liquid biological sample, the syringe or other sampling device can be configured as a container suitable for use in the embodiments herein. By way of example, referring now to FIG. 13 a schematic diagram of a container 1300 is shown in accordance with various embodiments herein. Container 1300 includes a syringe barrel 1302, a syringe plunger 1304, a needle 1306, and a chemical sensor element 308. In some embodiments, the container 1300 can include a needle coupling 1308 disposed between the syringe barrel 1302 and needle 1306. The needle 1306 can be inserted into a subject to remove a liquid biological sample 306. The liquid biological sample 306 can be drawn through the needle 1306 and into the syringe barrel 1302.

The container 1300 can be configured to include a chemical sensor element 308 to analyze the VOC emissions of a liquid biological sample 306. In this embodiment, the syringe plunger 1304 includes a chemical sensor element on the face of the syringe plunger 1304 disposed within the headspace 510 of syringe barrel 1302. Thus, in some embodiments, analysis of the liquid biological sample 306 can occur immediately after removal from a subject. In other embodiments, the liquid biological sample 306 can be allowed to incubate within the syringe barrel 1302 for a period of time to allow for emission of VOCs into the headspace 510 to equilibrate with the liquid biological sample 306. In some embodiments, the syringe plunger 1304 can be adjusted to increase or decrease the volume of gas in headspace 510.

Figures 13, 14:
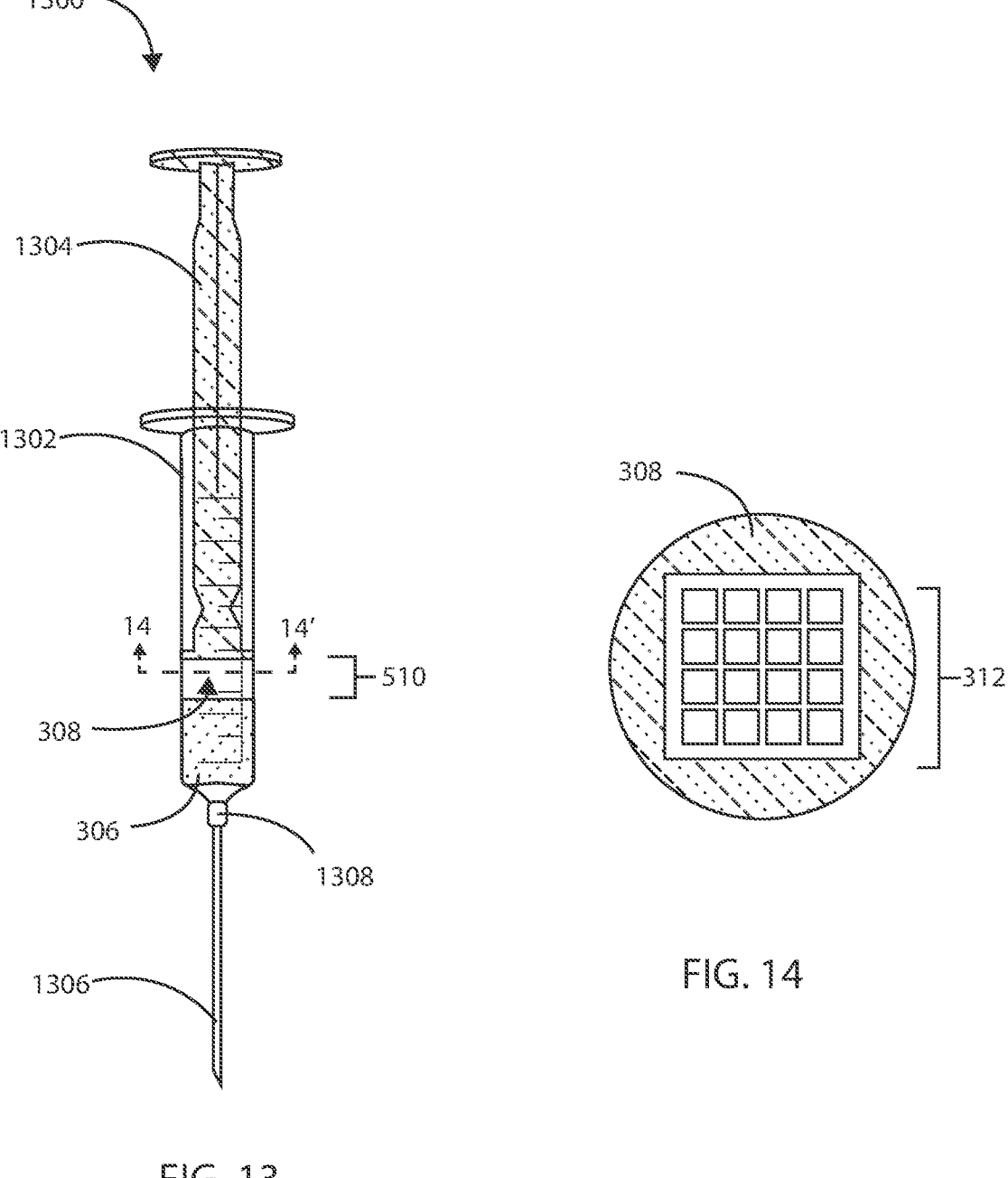
FIG. 13 is a schematic diagram of an additional embodiment of a container system in accordance with various embodiments herein.
FIG. 14 is a schematic view of the container of FIG. 13 from line 14-14' in accordance with various embodiments herein.

A schematic view of the chemical sensor element 308 disposed on the interior face of the syringe plunger 1304 of FIG. 13 from line 14-14' is shown in FIG. 14 in accordance with various embodiments herein. The chemical sensor element 308 can include an array of discrete graphene varactors 312 for sensing and storing capacitance of each of the discrete graphene varactors in response to binding by one or more biomarkers. It will be appreciated that the chemical sensor element 308 having a plurality of discrete graphene varactors disposed thereon can come in many shapes and sizes, as will be discussed below in reference to FIGS. 18-22.

Figures 15, 16:
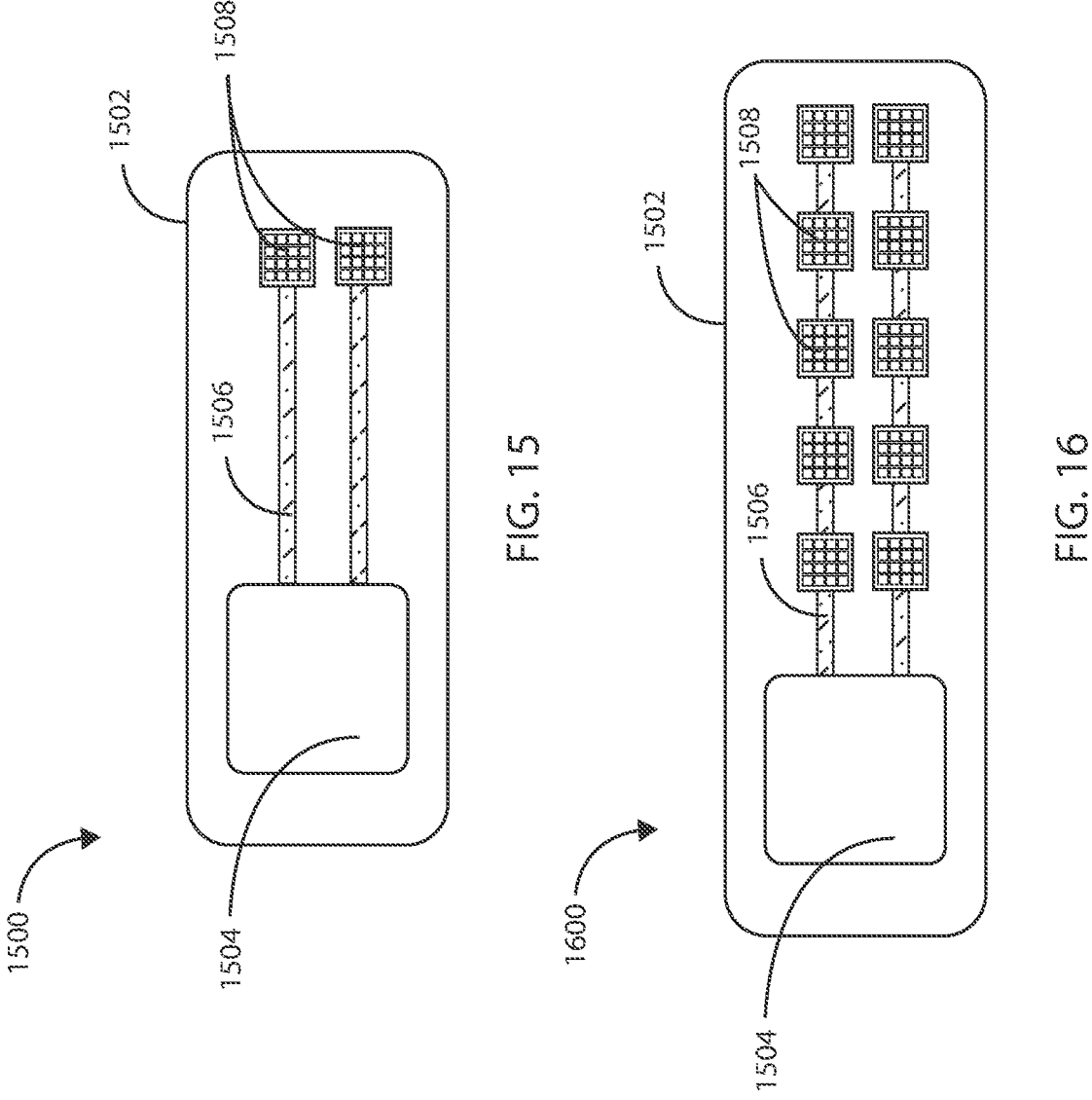
FIG. 15 is a schematic diagram of an additional embodiment of a container system in accordance with various embodiments herein.
FIG. 16 is a schematic diagram of an additional embodiment of a container system in accordance with various embodiments herein.

The container systems herein can include those that operate as a microfluidic chip. Referring now to FIG. 15, a schematic diagram of a container system 1500 is shown in accordance with various embodiments herein. Container system 1500 includes a housing 1502, a load reservoir 1504, one or more microchannels 1506 each in fluid communication with a chemical sensor element 1508. A liquid biological sample can be loaded into the load reservoir 1504 and the liquid biological sample can travel through the one or more microchannels 1506 via capillary action toward the chemical sensor element 1508. In some embodiments, the load reservoir 1504 of container system 1500 can be submersed into a liquid biological sample for a period of time such that the liquid biological sample can travel through the one or more microchannels 1506 via capillary action. In some embodiments the fluid flow of the liquid biological sample can be passive while in other embodiments the fluid flow of the liquid biological sample can be active. The container system 1500 includes a load reservoir 1504 that is in fluid communication with two microchannels 1506, where the two microchannels are in fluid communication with and that terminate at two chemical sensor elements 1508.

Referring now to FIG. 16, a schematic diagram of a container system 1600 is shown in accordance with various embodiments herein. Container system 1600 includes a housing 1502, a load reservoir 1504, one or more microchannels 1506, and wherein each of the microchannels 1506 is in fluid communication with a plurality of chemical sensor elements 1508. A liquid biological sample can be loaded into the load reservoir 1504 and the liquid biological sample can travel through the one or more microchannels 1506 via capillary action toward the plurality of chemical sensor elements 1508.

In some embodiments, the load reservoir 1504 of container system 1600 can be submersed into a liquid biological sample for a period of time such that the liquid biological sample can travel through the one or more microchannels 1506 via capillary action. In some embodiments the fluid flow of the liquid biological sample can be passive while in other embodiments the fluid flow of the liquid biological sample can be active. The container system 1600 includes a load reservoir 1504 that is in fluid communication with two microchannels 1506, where the two microchannels are in fluid communication with and that terminate at two chemical sensor elements 1508.

In some embodiments, the container systems 1500 and 1600 can include one, two, three, four, or more microchannels 1506. The one, two, three, or four microchannels 1506 can be in fluid communication with one, two, three, four, five, six, seven, eight, nine, ten, or more chemical sensor elements 1508.

Figure 17:
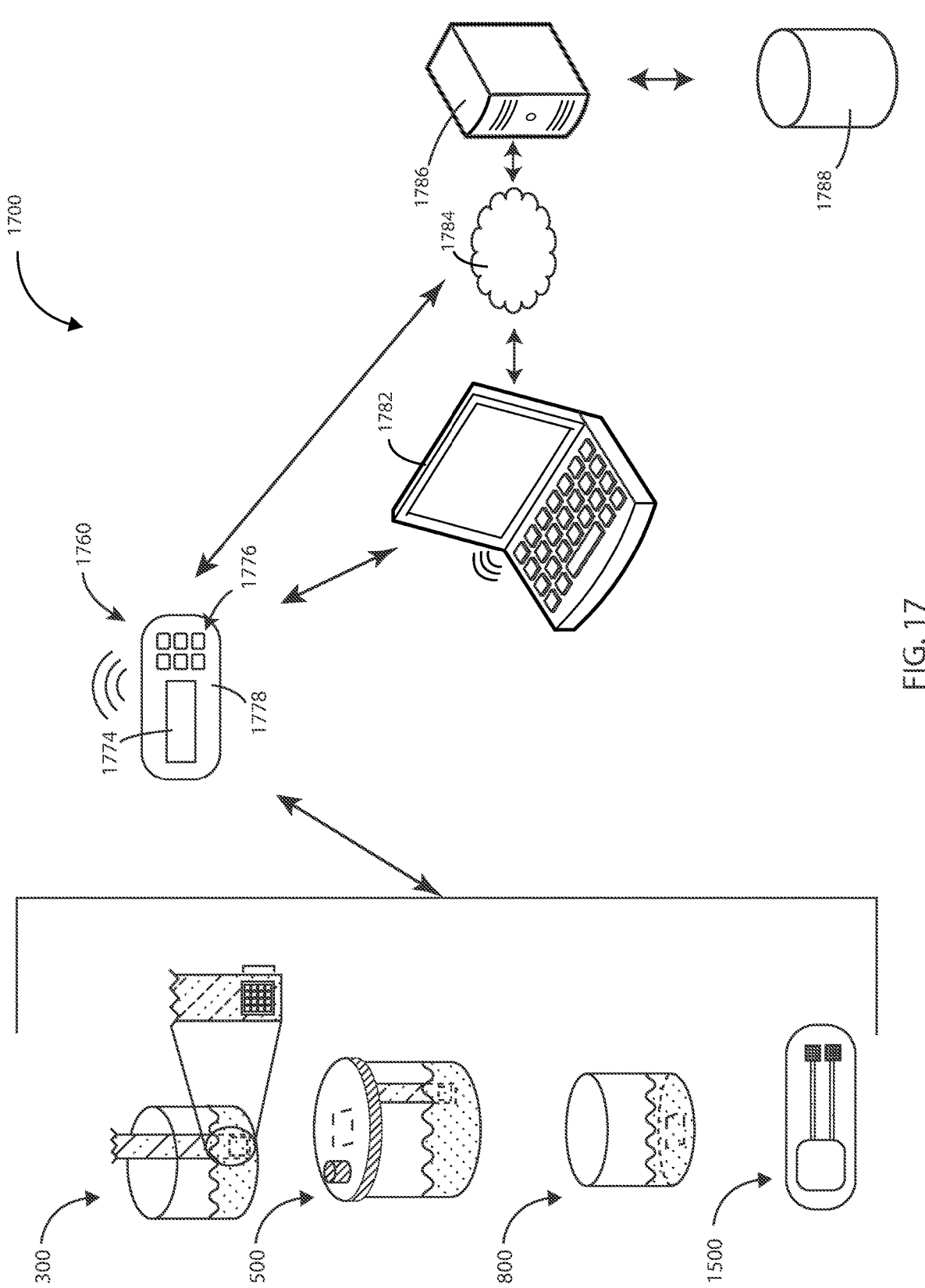
FIG. 17 is a schematic view of various components of a system in accordance with various embodiments herein.

The containers herein can interface with a system for sensing a capacitance in the plurality of graphene varactors. Referring now to FIG. 17, a schematic view is shown of components of a system 1700 in accordance with various embodiments herein. The system 1700 can include any of the container systems described herein, such as for example container systems 300, 500, 800, and 1500, and a sensing device 1760. In the embodiment in FIG. 17, the sensing device 1760 of system 1700 is in a hand-held format that can be used in the field. The sensing device 1760 can be a smart phone, tablet, or computer. It will be appreciated, however, that many other formats for the sensing device 1760 and system 1700 are contemplated herein that can utilize any combination of wireless and wired technology. In various embodiments, the sensing device can be configured to interface with the first chemical sensor element. The sensing device further can be configured to sense a capacitance of the plurality of discrete graphene varactors.

The sensing device 1760 can include a display screen 1774, a user input interface 1776, such as a keyboard, and a housing 1778. Aspects of sensing systems and devices are described in U.S. Patent Application Publication No. 2016/0109440, filed on Oct. 15, 2015, the content of which is herein incorporated by reference. The sensing device can include any of the circuitry described in reference to FIGS. 20 and 21 configured to interface with the chemical sensor elements as described herein.

In some embodiments, the system 1700 can include a local computing device 1782 that can include a microprocessor, input and output circuits, input devices, a visual display, one or more user interface devices, and the like. In some embodiments, the sensing device 1760 can communicate with the local computing device 1782 in order to exchange data between the sensing device 1760 and the local computing device 1782. The local computing device 1782 can be configured to perform various processing steps with the data received from the sensing device 1760, including, but not limited to, calculating various parameters described herein. However, it should be appreciated that in some embodiments the features associated with the local computing device 1782 can be integrated into the sensing device 1760. In some embodiments, the local computing device 1782 can be a laptop computer, a desktop computer, a server (real or virtual), a purpose dedicated computer device, or a portable computing device (including, but not limited to, a mobile phone, tablet, wearable device, etc.). The local computing device 1782 and/or the sensing device 1760 can communicate with computing devices in remote locations through a data network 1784, such as the Internet or another network for the exchange of data as packets, frames, or otherwise.

In some embodiments, the system 1700 can also include a computing device such as a server 1786 (real or virtual). The sensing device 1760 can be configured to communicate with server 1786 through the data network 1784. In some embodiments, the server 1786 can be located remotely from the sensing device 1760. The server 1786 can be in data communication with a database 1788. The database 1788 can be used to store various subject information, such as that described herein. In some embodiments, the database can specifically include an electronic medical database containing data regarding the health status of a subject, patterns of data associated with various conditions (such as that generated from machine learning analysis of large sets of subject data), demographic data and the like. In some embodiments, the database 1788 and/or server 1786, or a combination thereof, can store the data generated by the chemical sensor (s) as well as data output generated by machine learning analysis.

Figure 18:
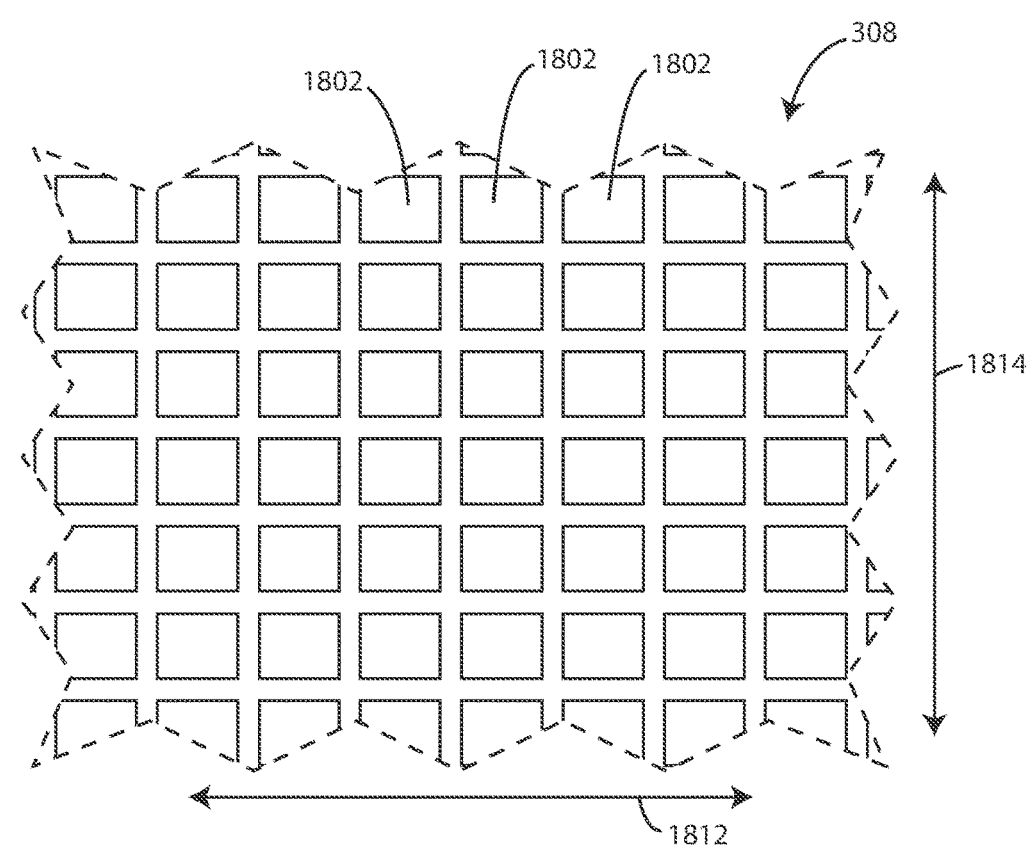
FIG. 18 is a schematic diagram of a portion of a chemical sensor element in accordance with various embodiments herein.

Referring now to FIG. 18, a schematic diagram of a portion of a chemical sensor element 308 is shown in accordance with various embodiments herein. A plurality of discrete graphene varactors 1802 can be disposed on the chemical sensor element 308 in an array. In some embodiments, a chemical sensor element can include a plurality of discrete graphene varactors configured in an array. In some embodiments, the plurality of discrete graphene varactors can be identical, while in other embodiments the plurality of discrete graphene varactors can be different from one another. The discrete graphene varactors herein can be as described in more detail in U.S. Pat. No. 9,513,244, filed on Jan. 3, 2014, the contents of which is herein incorporated by reference in its entirety.

The discrete graphene varactors can include those with surface modifications of a graphene surface. The surface modifications of the discrete graphene varactors can be configured to detect one or more biomarkers of a disease state. The surface modifications can include those that detect biomarkers including DNA, RNA, nucleolin, tumor cells, cell surface receptor proteins, C-reactive protein, transcription factors, cytokines, volatile organic compounds, exosomes, or derivatives and fragments thereof.

In some embodiments, the discrete graphene varactors can be heterogeneous in that they are different (in groups or as individual discrete graphene varactors) from one another in terms of their binding behavior or specificity with regard a particular biomarker. In some embodiments, some discrete graphene varactors can be duplicated for validation purposes but are otherwise heterogeneous from other discrete graphene varactors. Yet in other embodiments, the discrete graphene varactors can be homogeneous in terms of a binding behavior or a specificity with regard a particular biomarker. While the discrete graphene varactors 1802 of FIG. 18 are shown as boxes organized into a grid, it will be appreciated that the discrete graphene varactors can take on many different shapes (including, but not limited to, various polygons, circles, ovals, irregular shapes, and the like) and, in turn, the groups of discrete graphene varactors can be arranged into many different patterns (including, but not limited to, star patterns, zig-zag patterns, radial patterns, symbolic patterns, and the like).

In some embodiments, the order of specific discrete graphene varactors 1802 across the length 1812 and width 1814 of the measurement zone can be substantially random. In other embodiments, the order can be specific. For example, in some embodiments, a measurement zone can be ordered so that the specific discrete graphene varactors 1802 for biomarkers having a lower molecular weight are located farther away from the incoming gas flow relative to specific discrete graphene varactors 1802 for biomarkers having a higher molecular weight which are located closer to the incoming gas flow. As such, chromatographic effects which may serve to provide separation between chemical compounds of different molecular weight can be taken advantage of to provide for optimal binding of chemical compounds to corresponding discrete graphene varactors.

The number of discrete graphene varactors can be from about 1 to about 100,000. In some embodiments, the number of discrete graphene varactors can be from about 1 to about 10,000. In some embodiments, the number of discrete graphene varactors can be from about 1 to about 1,000. In some embodiments, the number of discrete graphene varactors can be from about 2 to about 500. In some embodiments, the number of discrete graphene varactors can be from about 10 to about 500. In some embodiments, the number of discrete graphene varactors can be from about 50 to about 500. In some embodiments, the number of discrete graphene varactors can be from about 1 to about 250. In some embodiments, the number of discrete graphene varactors can be from about 1 to about 50.

In some embodiments, each of the discrete graphene varactors suitable for use herein can include at least a portion of one or more electrical circuits. By way of example, in some embodiments, each of the discrete graphene varactors can include all or a portion of one or more passive electrical circuits. In some embodiments, the graphene varactors can be formed such that they are integrated directly on an electronic circuit. In some embodiments, the graphene varactors can be formed such that they are wafer bonded to the circuit. In some embodiments, the graphene varactors can include integrated readout electronics, such as a readout integrated circuit (ROIC). The electrical properties of the electrical circuit, including resistance or capacitance, can change upon binding, such as specific and/or non-specific binding, with a component from a liquid biological sample. Many different types of circuits can be used to gather data from chemical sensor elements and will be discussed below in reference to FIGS. 18 and 19.

Figure 19:
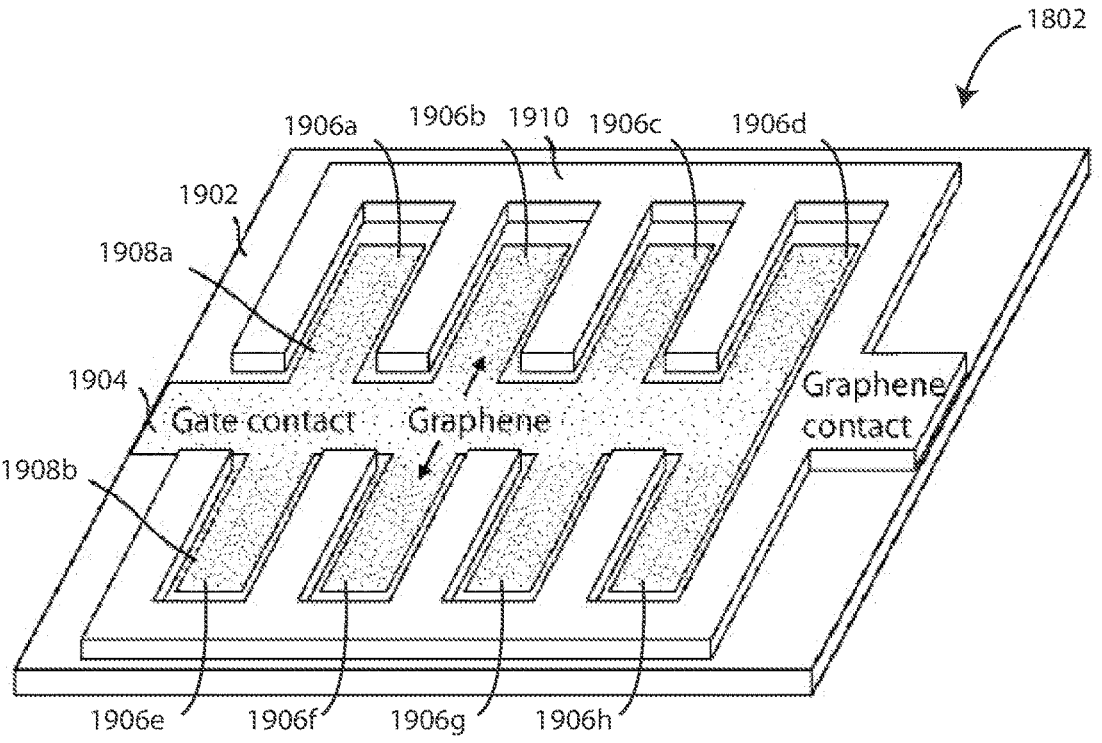
FIG. 19 is a schematic perspective view of a discrete graphene varactor in accordance with various embodiments herein.

In some embodiments, the discrete graphene varactors embodied herein can include graphene-based variable capacitors (or graphene varactors). Referring now to FIG. 19, a schematic view of a discrete graphene varactor 1802 is shown in accordance with the embodiments herein. It will be appreciated that discrete graphene varactors can be prepared in various ways with various geometries, and that the discrete graphene varactor shown in FIG. 19 is just one example in accordance with the embodiments herein.

Discrete graphene varactor 1802 can include an insulator layer 1902, a gate electrode 1904 (or "gate contact"), a dielectric layer (not shown in FIG. 19), one or more graphene layers, such as graphene layers 1908a and 1908b, and a contact electrode 1910 (or "graphene contact"). In some embodiments, the graphene layer(s) 1908a-b can be contiguous, while in other embodiments the graphene layer(s) 1908a-b can be non-contiguous. Gate electrode 1904 can be deposited within one or more depressions formed in insulator layer 1902. Insulator layer 1902 can be formed from an insulative material such as silicon dioxide, formed on a silicon substrate (wafer), and the like. Gate electrode 1904 can be formed by an electrically conductive material such as chromium, copper, gold, silver, tungsten, aluminum, titanium, palladium, platinum, iridium, and any combinations or alloys thereof, which can be deposited on top of or embedded within the insulator layer 1902. The dielectric layer can be disposed on a surface of the insulator layer 1902 and the gate electrode 1904. The graphene layer(s) 1908a-b can be disposed on the dielectric layer.

Discrete graphene varactor 1802 includes eight gate electrode fingers 1906a-1906h. It will be appreciated that while discrete graphene varactor 1802 shows eight gate electrode fingers 1906a-1906h, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Discrete graphene varactor 1802 can include one or more contact electrodes 1910 disposed on portions of the graphene layers 1908a and 1908b. Contact electrode 1910 can be formed from an electrically conductive material such as chromium, copper, gold, silver, tungsten, aluminum, titanium, palladium, platinum, iridium, and any combinations or alloys thereof. Further aspects of exemplary graphene varactors can be found in U.S. Pat. No. 9,513,244, filed on Jan. 3, 2014, the content of which is herein incorporated by reference in its entirety.

The capacitance of the graphene varactors can be measured by delivering an excitation current at a particular voltage and/or over a range of voltages. Measuring the capacitance provides data that reflects the binding status of biomarkers to the graphene varactor(s). Various measurement circuitry can be used to measure the capacitance of the graphene varactor(s).

Figure 20:
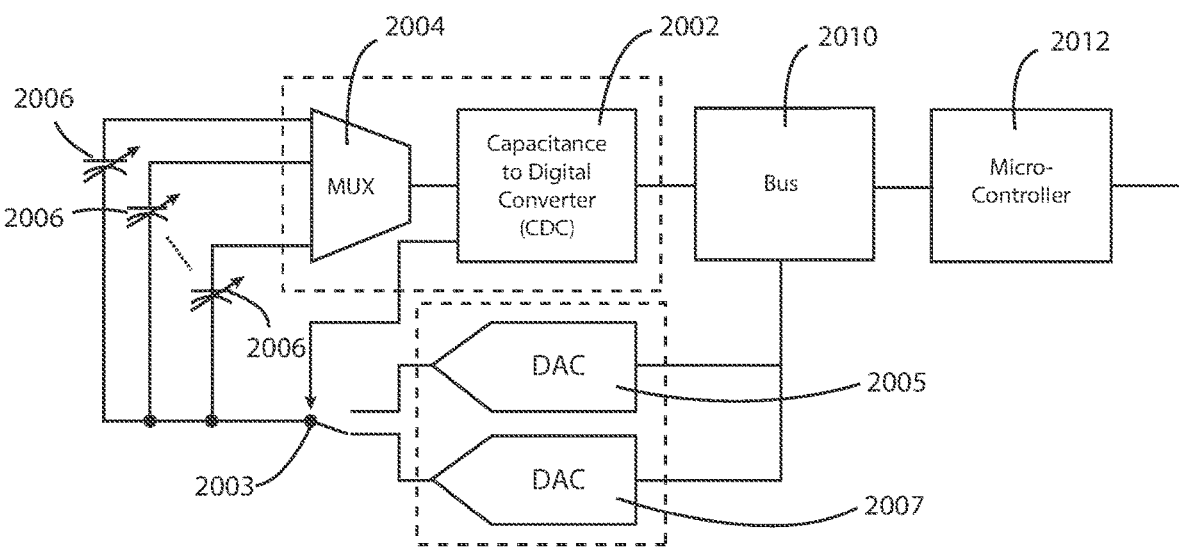
FIG. 20 is a schematic diagram of circuitry to measure the capacitance of a plurality of discrete graphene varactors in accordance with various embodiments herein.

Referring now to FIG. 20, a schematic diagram is shown of circuitry to measure the capacitance of a plurality of discrete graphene varactors in accordance with various embodiments herein. The circuitry can include a capacitance to digital converter (CDC) 2002 in electrical communication with a multiplexor 2004. The multiplexor 2004 can provide selective electrical communication with a plurality of graphene varactors 2006. The connection to the other side of the graphene varactors 2006 can be controlled by a switch 2003 (as controlled by the CDC) and can provide selective electrical communication with a first digital to analog converter (DAC) 2005 and a second digital to analog converter (DAC) 2007. The other side of the DACs 2005, 2007 can be connected to a bus device 2010, or in some cases, the CDC 2002. The circuitry can further include a microcontroller 2012, which will be discussed in more detail below.

In this case, the excitation signal from the CDC controls the switch between the output voltages of the two programmable Digital to Analog Converters (DACs). The programmed voltage difference between the DACs determines the excitation amplitude, providing an additional programmable scale factor to the measurement and allowing measurement of a wider range of capacitances than specified by the CDC. The bias voltage at which the capacitance is measured is equal to the difference between the bias voltage at the CDC input (via the multiplexor, usually equal to VCC/2, where VCC is the supply voltage) and the average voltage of the excitation signal, which is programmable. In some embodiments, buffer amplifiers and/or bypass capacitance can be used at the DAC outputs to maintain stable voltages during switching. Many different ranges of DC bias voltages can be used. In some embodiments, the range of DC bias voltages can be from −3 V to 3 V, or from −1 V to 1 V, or from −0.5 V to 0.5 V.

Many different aspects can be calculated based on the capacitance data. For example, aspects that can be calculated include maximum slope of capacitance to voltage, change in maximum slope of capacitance to voltage over a baseline value, minimum slope of capacitance to voltage, change in minimum slope of capacitance to voltage over a baseline value, minimum capacitance, change in minimum capacitance over a baseline value, voltage at minimum capacitance (Dirac point), change in voltage at minimum capacitance, maximum capacitance, change in maximum capacitance, ratio of maximum capacitance to minimum capacitance, response time constants, and ratios of any of the foregoing between different discrete graphene varactors and particularly between different discrete graphene varactors having specificity for different biomarkers.

The above calculated aspects can be used for various diagnostic purposes. In some cases, the above calculated aspects can be indicative of the identity and/or concentrations of specific volatile organic components of a gas sample. As such, each of the calculated values above can serve as a distinct piece of data that forms part of a pattern for a given subject and/or given gas sample. As also described elsewhere herein, the pattern can then be matched against preexisting patterns, or patterns identified in real-time, derived from large stored data sets through techniques such as machine learning or other techniques, wherein such patterns are determined to be characteristic of various conditions or disease states. The above calculated aspects can also be put to other purposes, diagnostic and otherwise.

In some embodiments, calculations such as those described above can be performed by a controller circuit. The controller circuit can be configured to receive an electrical signal reflecting the capacitance of the graphene varactors. In some embodiments, the controller circuit can include a microcontroller to perform these calculations. In some embodiments, the controller circuit can include a microprocessor in electrical communication with the measurement circuit. The microprocessor system can include components such as an address bus, a data bus, a control bus, a clock, a CPU, a processing device, an address decoder, RAM, ROM and the like. In some embodiments, the controller circuit can include a calculation circuit (such as an application specific integrated circuit—ASIC) in electrical communication with the measurement circuit.

In addition, in some embodiments, the system can include a nonvolatile memory where sensitivity calibration information for the particular sensor is stored. By way of example, the sensor could be tested in a production facility, where its sensitivity to various biomarkers, such as VOCs, can be determined and then stored on an EPROM or similar component. In addition, or alternatively, sensitivity calibration information can be stored in a central database and referenced with a sensor serial number when subject data is sent to a central location for analysis and diagnosis. These components can be included with any of the pieces of hardware described herein.

In some embodiments herein, components can be configured to communicate over a network, such as the internet or a similar network. In various embodiments, a central storage and data processing facility can be included. In some embodiments, data gathered from sensors in the presence of the subject (local) can be sent to the central processing facility (remote) via the internet or a similar network, and the pattern from the particular subject being evaluated can be compared to those of thousands or millions of other subjects, many of whom have been previously diagnosed with various conditions and wherein such condition data has been stored. Pattern matching algorithms can be used to find other subjects or classes of subjects (for example disease or condition specific classes) to which the current subject's pattern is most similar. Each class of subjects can include a predetermined likelihood of having a given condition or disease state. In this manner, after pattern matching a likelihood of having a given condition or disease state can be provided back across the data network to the facility where the subject is currently located.

Figure 21:
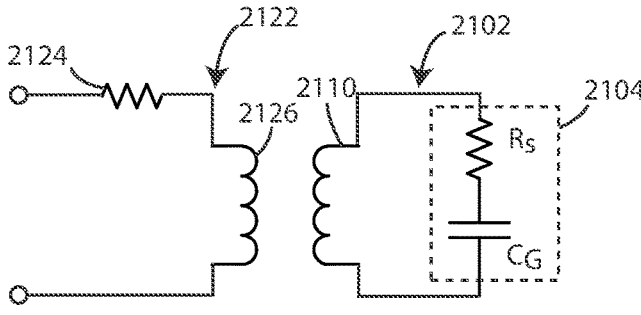
FIG. 21 is a schematic diagram of a passive sensor circuit and a portion of a reading circuit is shown in accordance with various embodiments herein.

In some embodiments, circuitry can include active and passive sensing circuits. Such circuitry can implement wired (direct electrical contact) or wireless sensing techniques. Referring now to FIG. 21, a schematic diagram of a passive sensor circuit 2102 and a portion of a reading circuit 2122 is shown in accordance with various aspects herein. In some embodiments, the passive sensor circuit 2102 can include a metal-oxide-graphene varactor 2104 (wherein RS represents the series resistance and CG represents the varactor capacitor) coupled to an inductor 2110. In some embodiments, the reading circuit 2122 can include a reading coil having a resistance 2124 and an inductance 2126. However, it will be appreciated that the circuits shown in FIGS. 15 and 16 are merely exemplary approaches. Many different approaches are contemplated herein.

Figure 22:
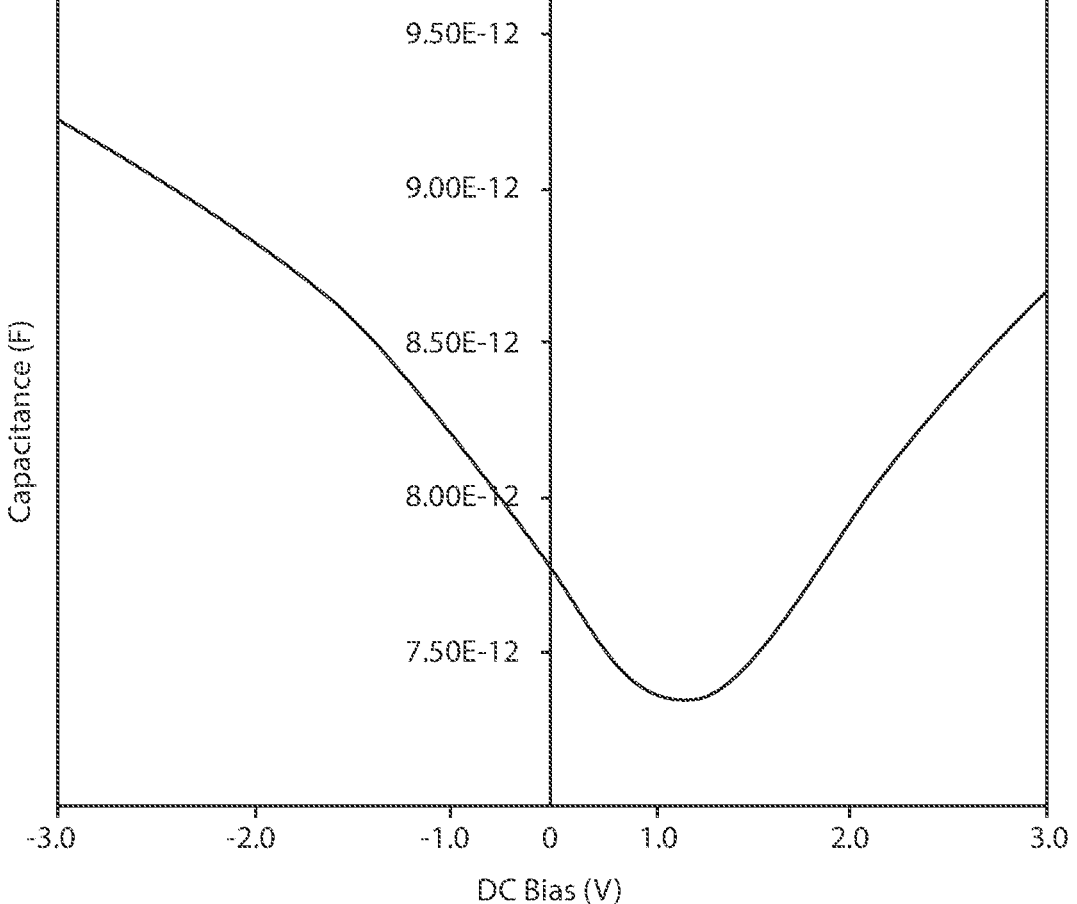
FIG. 22 is a graph showing capacitance versus DC bias voltage for a discrete graphene varactor in accordance with various embodiments herein.

Referring now to FIG. 22 an exemplary graph showing capacitance versus DC bias voltage for a graphene varactor is shown in accordance with various embodiments herein. A capacitance to voltage curve like that shown in FIG. 22 can be established by measuring capacitance over a range of bias voltages while exposing the chemical sensor to the gas emitted from a liquid biological sample of a subject using circuits such as those described in FIGS. 15 and 16. In some embodiments, the range of bias voltages can include from –3 V to 3 V. In some embodiments, the range of DC bias voltages can be from –2 V to 2 V, or from –1.5 V to 1.5 V, or from –1 V to 1 V, or from –0.5 V to 0.5 V.

Additional Methods

Figure 23:
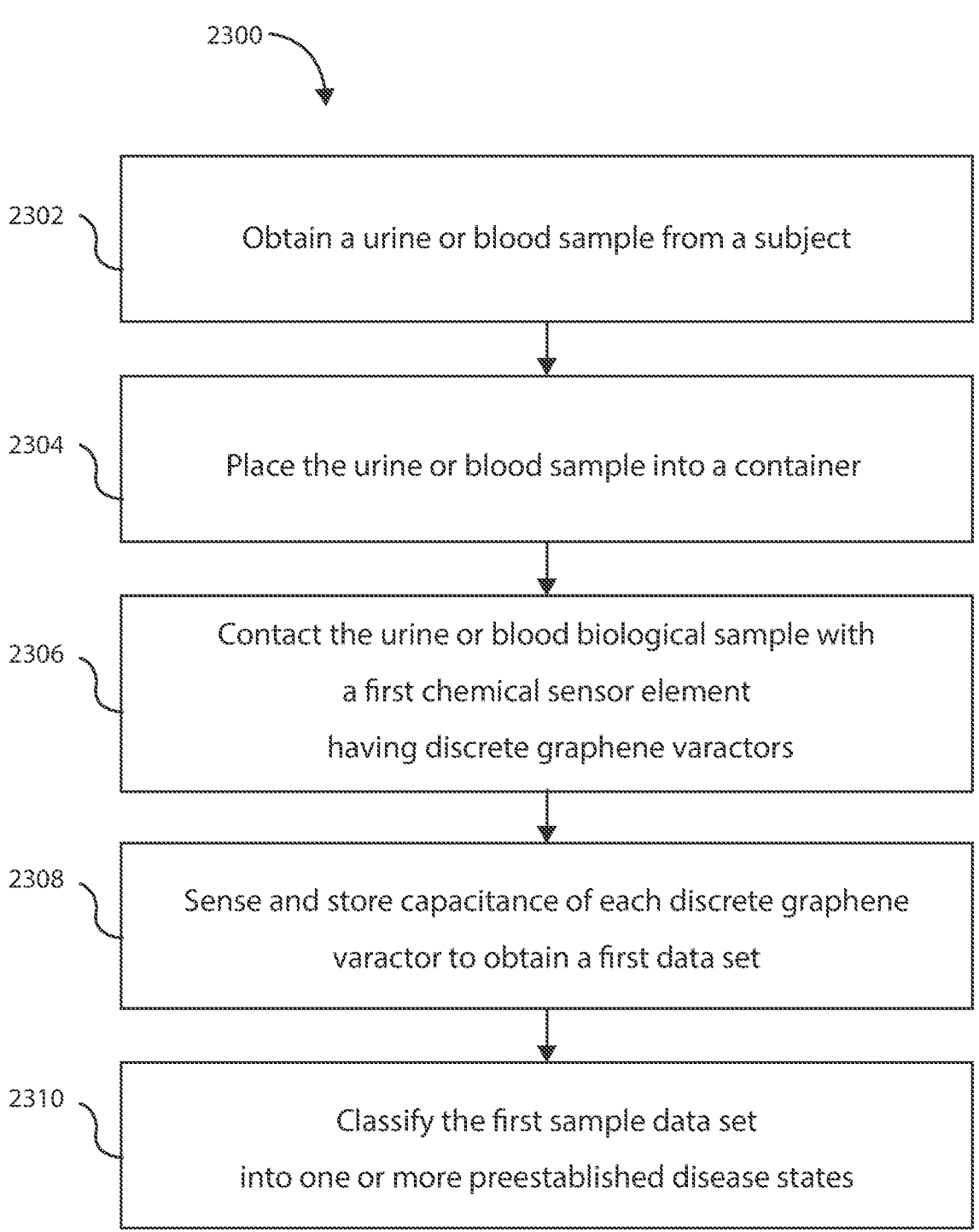
FIG. 23 is a schematic flow diagram of an additional method for detecting a health condition in accordance with various embodiments herein.

Additional methods herein can be directed to a specific disease state, such as bladder cancer. Referring now to FIG. 23, a schematic view of a method 2300 for detecting a disease state in a subject is shown in accordance with various embodiments herein. The method 2300 can include a method for detecting bladder cancer in a subject. Method 2300 can include obtaining a urine or blood sample from the subject at 2302. The method can include placing the liquid biological sample into a container at 2304. The method 2300 can include contacting the urine or blood sample with a first chemical sensor element at 2306, where the first chemical sensor element includes a plurality of discrete graphene varactors. The method can include sensing and storing capacitance of each of the discrete graphene varactors to obtain a first sample data set at 2308. The method can further include classifying the first sample data set into one or more preestablished disease states at 2310. In various embodiments, the method 2300 can include classifying the first sample data set into one or more preestablished disease states including stage I bladder cancer, stage II bladder cancer, stage III bladder cancer, or stage IV bladder cancer.

Liquid Biological Sample Handling

It will be appreciated that various liquid biological sample collection, processing, and storage techniques can be employed when obtaining the liquid biological sample from a subject in accordance with the embodiments herein. Liquid biological samples can be obtained from a subject using invasive or non-invasive collection methods. The collection methods can include minimally invasive sample collection from the subject, such as in the case of urine collection and a blood draw, or the like. In some embodiments, the liquid biological sample is minimally processed and in other embodiments the liquid biological sample is not processed at all. In some embodiments, a tumor sample can be obtained and processed into a liquid suspension.

Once a liquid biological sample has been obtained from a subject and placed into a container, the liquid biological sample can be stored for future use or it can be used immediately. In some embodiments, the liquid biological sample can be incubated for a predetermined amount of time at a predetermined temperature and humidity. During incubation, the liquid biological sample can be heated with a heat source to maintain the sample within a given temperature range. In some embodiments, the temperature range can include a physiological temperature range, such as 35 degrees Celsius (° C.) to 39° C. While in some embodiments the liquid biological sample can be maintained at physiological temperature, in other embodiments the liquid biological sample can be maintained at temperatures outside the physiological range. For example, the liquid biological sample can be maintained at a temperature from about 10° C. to about 30° C. In other embodiments, the liquid biological sample can be maintained at a temperature from 25° C. to 40° C. In other embodiments, the liquid biological sample can be maintained at a temperature from 40° C. to 50° C. In some embodiments, the liquid biological sample can be aerated with an inert gas. By way of example, a liquid biological sample can be aerated in a stepwise fashion over a given time period.

Classification and Pattern Matching

Classifying the sample data set into one or more preestablished disease classifications can be performed according to many different machine learning techniques, such as pattern recognition. Classification can include comparing the sample data set against one or more previously determined patterns using a pattern matching or pattern recognition algorithm to determine the pattern that is the best match, wherein the specific previously determined pattern that is the best match indicates the disease state of the subject.

By way of example, patterns amongst large sets of subject data may be originally identified through machine learning analysis or another similar algorithmic technique. Patterns associated with specific disease state classifications can be derived from labeled "training" data (supervised learning) or in the absence of labeled data (unsupervised learning).

Algorithms for pattern matching used herein can include, but are not limited to, classification algorithms (supervised algorithms predicting categorical labels), clustering algorithms (unsupervised algorithms predicting categorical labels), ensemble learning algorithms (supervised meta-algorithms for combining multiple learning algorithms together), general algorithms for predicting arbitrarily-structured sets of labels, multilinear subspace learning algorithms (predicting labels of multidimensional data using tensor representations), real-valued sequence labeling algorithms (predicting sequences of real-valued labels), regression algorithms (predicting real-valued labels), and sequence labeling algorithms (predicting sequences of categorical labels).

Classification algorithms can include parametric algorithms (such as linear discriminant analysis, quadratic discriminant analysis, and maximum entropy classifier) and nonparametric algorithms (such as decision trees, kernel estimation, naïve Bayes classifier, neural networks, perceptrons, and support vector machines). Clustering algorithms can include categorical mixture models, deep learning methods, hierarchical clustering, K-means clustering, correlation clustering, and kernel principal component analysis. Ensemble learning algorithms can include boosting, bootstrap aggregating, ensemble averaging, and mixture of experts. General algorithms for predicting arbitrarily structured sets of labels can include Bayesian networks and Markov random fields. Multilinear subspace learning algorithms can include multilinear principal component analysis (MPCA). Real-valued sequence labeling algorithms can include Kalman filters and particle filters. Regression algorithms can include both supervised (such as Gaussian process regression, linear regression, neural networks and deep learning methods) and unsupervised (such as independent component analysis and principal components analysis) approaches. Sequence labeling algorithms can include both supervised (such as conditional random fields, hidden Markov models, maximum entropy Markov models, and recurrent neural networks) and unsupervised (hidden Markov models and dynamic time warping) approaches.

Methods of Treating

Embodiments herein can specifically include methods of treating a disease state in a subject. The method can include obtaining a liquid biological sample from the subject and placing it into a container having a headspace above or around the liquid biological sample. The method can further include contacting the liquid biological sample and/or a gas within a headspace with a chemical sensor element, where the chemical sensor element includes a plurality of discrete graphene varactors. The method can further include sensing and storing capacitance of the discrete graphene varactors to obtain one or more sample data sets. The method can further include classifying the sample data set into one or more preestablished disease state classifications. The method can further include identifying a therapy to treat the subject based on the disease state classification.

By way of example, one exemplary set of classifications and possible treatments for a disease state are provided below in Table 1.

TABLE 1

| Disease State Classification | Treatment |
|---|---|
| No Indication of Disease State | No Treatment |
| Indication of Mild Disease State | Prescription Drug Therapy, OTC Drug Therapy, Minimally invasive surgical removal of a tumor, mass, or abscess |
| Indication of Severe Disease State | Drug Therapies Including One or More of: antibiotic agent, antineoplastic agent, chemotherapeutic agent Referral for Clinical Therapies Including One or More of: surgical removal of a tumor, mass, or abscess; radiation therapy; chemotherapy; immunotherapy; hormone therapy; ablation therapy; stem cell transplant; photodynamic therapy |

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A system for detecting a disease state comprising:
a container, the container comprising a plunger and a barrel, the barrel adapted to contain a liquid biological sample of a subject, the barrel defining a headspace comprising a volume of a gas;
a chemical sensor element positioned on the plunger, the chemical sensor configured to be contacted with the gas from the headspace above the liquid biological sample, the chemical sensor element comprising a plurality of discrete graphene varactors, wherein each of the plurality of discrete graphene varactors is configured to detect one or more biomarkers of the disease state; and
a sensing device configured to interface with the chemical sensor element, the sensing device further configured to sense a capacitance of the plurality of discrete graphene varactors in response to binding by the one or more biomarkers.

2. The system of claim 1, wherein the plurality of discrete graphene varactors are configured in an array.

3. The system of claim 1, the plurality of discrete graphene varactors each comprising one or more surface modifications of a graphene surface.

4. The system of claim 3, wherein the surface modifications of the plurality of discrete graphene varactors are configured to detect one or more biomarkers of a disease state, the biomarkers comprising DNA, RNA, nucleolin, tumor cells, cell surface receptor proteins, C-reactive protein, transcription factors, cytokines, volatile organic compounds, exosomes, or derivatives and fragments thereof.

* * * * *